US012740814B2

(12) United States Patent
Tiernan

(10) Patent No.: US 12,740,814 B2
(45) Date of Patent: Sep. 22, 2026

(54) BONE FIXATION DEVICE AND SYSTEM AND METHOD FOR USING THE DEVICE

(71) Applicant: DGT MEDICAL LIMITED, Limerick (IE)

(72) Inventor: David Tiernan, Limerick (IE)

(73) Assignee: DGT MEDICAL LIMITED, Limerick (IE)

( * ) Notice: Subject to any disclaimer, the term of this patent is extended or adjusted under 35 U.S.C. 154(b) by 228 days.

(21) Appl. No.: 18/258,132

(22) PCT Filed: Dec. 17, 2021

(86) PCT No.: PCT/EP2021/086656
§ 371 (c)(1),
(2) Date: Jun. 16, 2023

(87) PCT Pub. No.: WO2022/129614
PCT Pub. Date: Jun. 23, 2022

(65) Prior Publication Data

US 2024/0099748 A1 Mar. 28, 2024

Related U.S. Application Data

(60) Provisional application No. 63/126,652, filed on Dec. 17, 2020.

(51) Int. Cl.
*A61B 17/80* (2006.01)

(52) U.S. Cl.
CPC ...... *A61B 17/8052* (2013.01); *A61B 17/8014* (2013.01)

(58) Field of Classification Search
CPC ............ A61B 17/8004; A61B 17/8009; A61B 17/8014; A61B 17/8028; A61B 17/8047; A61B 17/8052; A61B 17/8085
See application file for complete search history.

(56) References Cited

U.S. PATENT DOCUMENTS 7,699,880 B2 * 4/2010 Orbay ................ A61B 17/8047 606/294
7,766,948 B1 * 8/2010 Leung ................ A61B 17/8052 606/291

(Continued)

FOREIGN PATENT DOCUMENTS

AU 2011202372 A1 12/2011
WO 2007149325 A2 12/2007
WO 2014057405 A1 4/2014

OTHER PUBLICATIONS

PCT International Search Report; Application No. PCT/EP2021/086656; Jun. 28, 2022; 6 pages.

(Continued)

*Primary Examiner* — Larry E Waggle, Jr.
(74) *Attorney, Agent, or Firm* — Conley Rose, P.C.; Brooks W Taylor

(57) ABSTRACT

The present disclosure relates to a system comprising a dynamic locking bone plate and screw that provide a plate and screw complex for fracture fixation. The plate comprises a plurality of screw holes, each screw hole adapted to receive a screw. The screw threads allow for insertion into bone with compression of the plate to bone and the four male components on the screw head allow for the screws to be locked into place in the plate once they interact with the female components of the plate. The screw locking heads will come in two form, one plush fit to the locking plate and the other offset to allow some movement in the screw plate complex. On the under surface of the plate, the plate comprises a raised area or protrusion defining the bone to plate contact surface. The area between adjacent screw holes is adapted to allow for customisation by the surgeon intra-operatively for optimal fracture fixation. The screw head comprises a tapered shoulder to allow for compression at the fracture site if placed in an eccentric position.

13 Claims, 28 Drawing Sheets

(56) References Cited

U.S. PATENT DOCUMENTS

| | | | | |
|---|---|---|---|---|
| 7,963,982 | B2 * | 6/2011 | Kirschman | A61B 17/8052 606/291 |
| 8,425,573 | B2 * | 4/2013 | Erickson | A61B 17/1728 606/104 |
| 8,496,692 | B2 * | 7/2013 | Bhatnagar | A61B 17/8052 606/289 |
| 8,764,808 | B2 * | 7/2014 | Gonzalez-Hernandez | A61B 17/8052 606/280 |
| 8,968,368 | B2 * | 3/2015 | Tepic | A61B 17/80 606/280 |
| 10,751,098 | B2 | 8/2020 | Gahman et al. | |
| 2008/0015592 | A1 * | 1/2008 | Long | A61B 17/8052 606/279 |
| 2008/0200955 | A1 | 8/2008 | Tepic | |
| 2009/0281543 | A1 | 11/2009 | Orbay et al. | |
| 2012/0197303 | A1 | 8/2012 | King et al. | |
| 2014/0214036 | A1 | 7/2014 | Weiner et al. | |
| 2015/0366595 | A1 | 12/2015 | Kaufmann et al. | |
| 2018/0256224 | A1 * | 9/2018 | Govey | A61B 17/8004 |
| 2020/0237418 | A1 * | 7/2020 | Courtney, Jr. | A61B 17/8057 |

OTHER PUBLICATIONS

PCT Written Opinion of the International Searching Authority; Application No. PCT/EP2021/086656; Jun. 28, 2022; 12 pages.

Burge, Russell, et al.; "Incidence and Economic Burden of Osteoporosis-Related Fractures in the United States, 2005-2025"; Journal of Bone and Mineral Research; vol. 22, No. 3; Dec. 4, 2006; 11 pages.

Ihealthcareanalyst, Inc.; "Global Fracture Fixation Products Market $15.2 Billion by 2029"; iHealthcareAnalyst, Inc.; Aug. 18, 2022; 6 pages.

Zura, Robert, et al.; "Epidemiology of Fracture Nonunion in 18 Human Bones"; JAMA Surgery; Sep. 7, 2016; 12 pages.

European Examination Report; Application No. 21836575.7; Mar. 19, 2025; 10 pages.

* cited by examiner 17
15
18
16

50
1
15
18
15

500
1
50
18
16

50
1
500
50
1

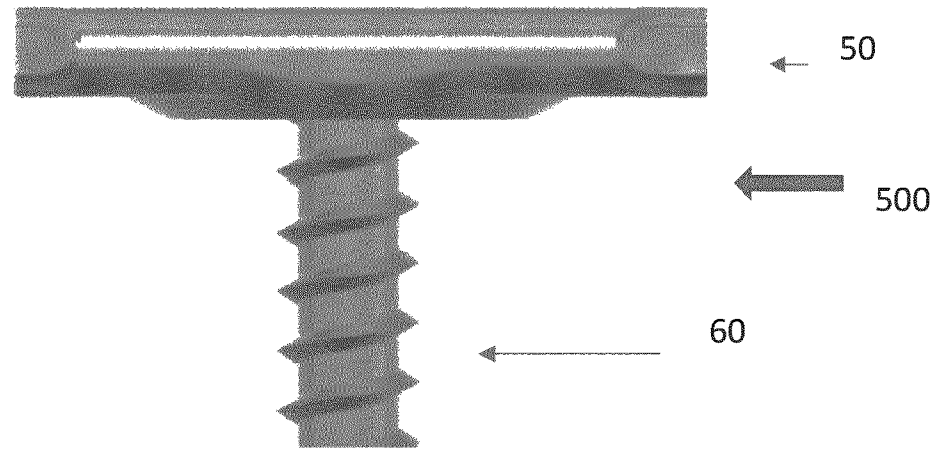
Fig 13
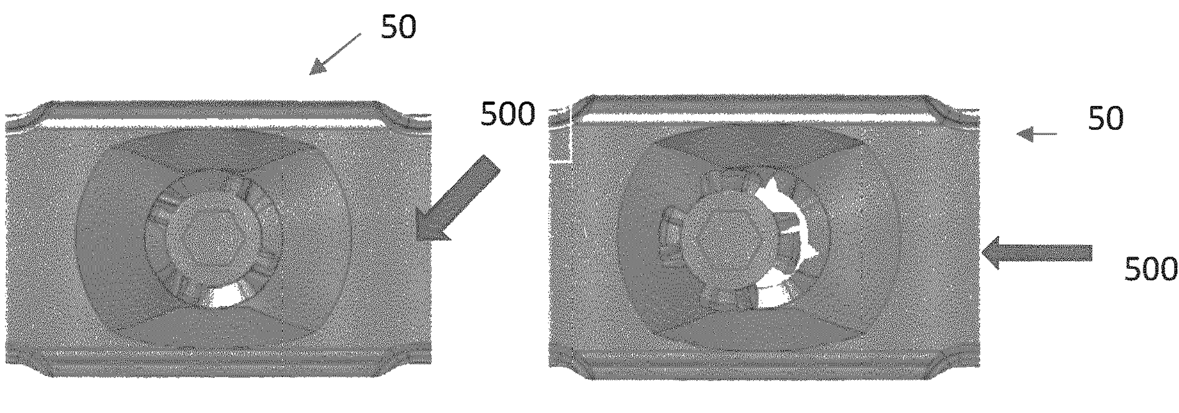
Fig 14
Fig 15
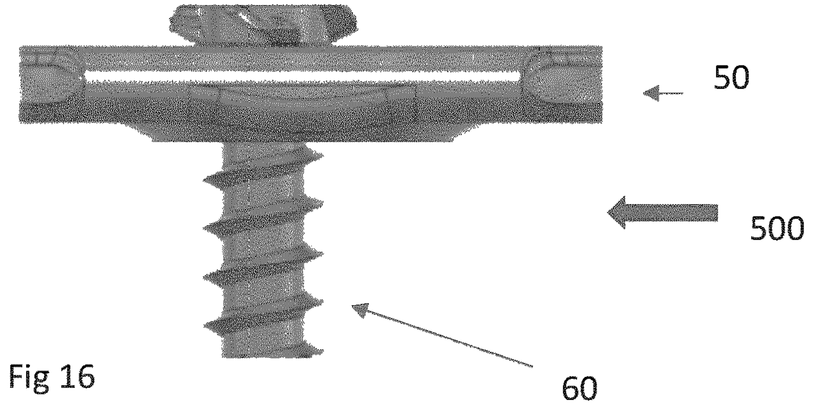
Fig 16

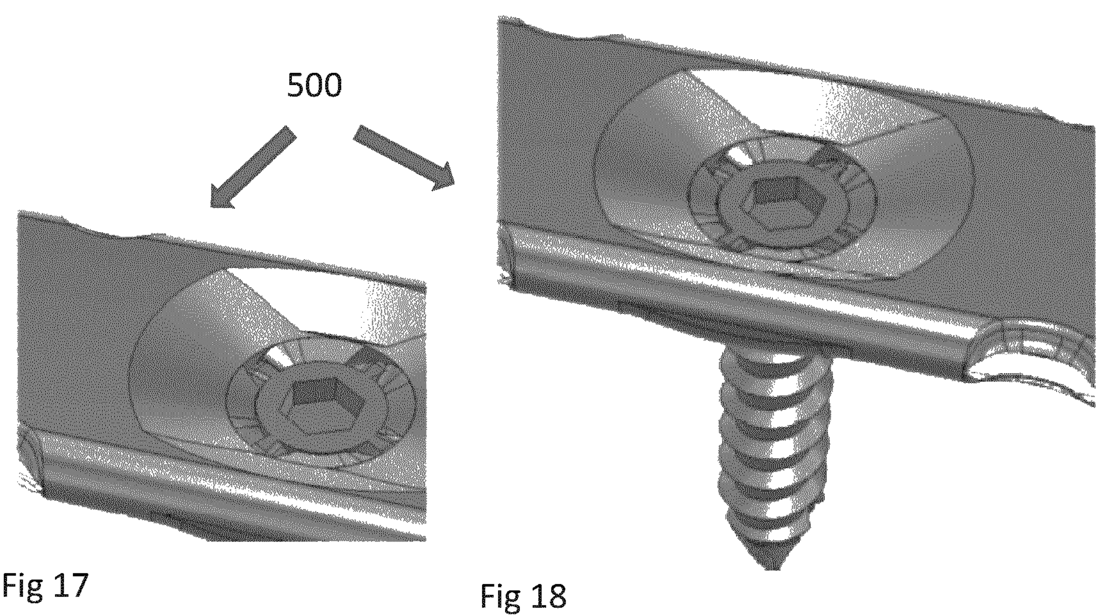
Fig 17
Fig 18
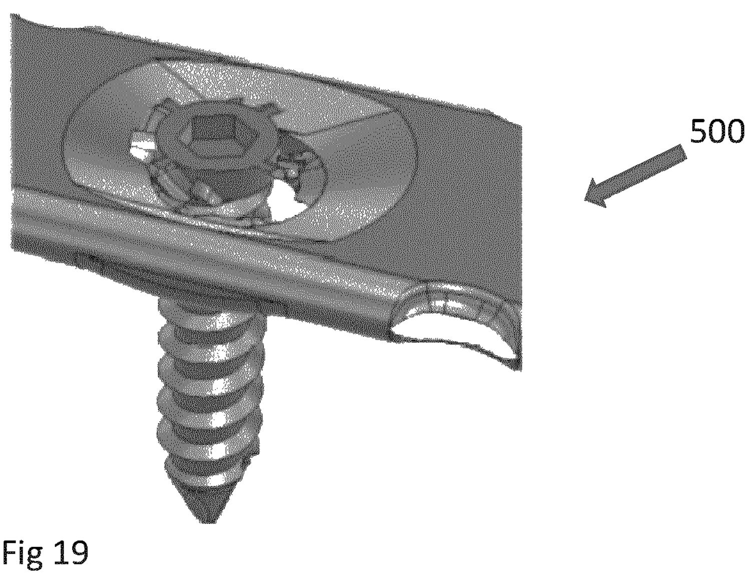
Fig 19

153
150
105
X-X
107
104
Z-Z
109
H1
H2
110
111
108
112
113
154
106

115
116
116-1
160
118
119
121
120
122
120

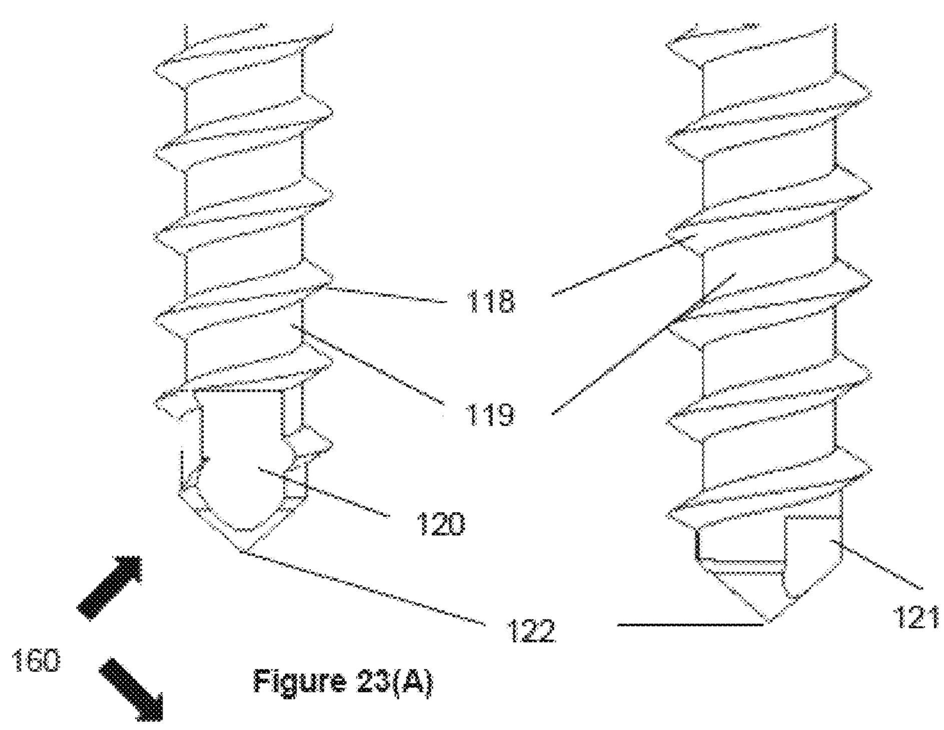
Figure 23(A)
Figure 23(B)
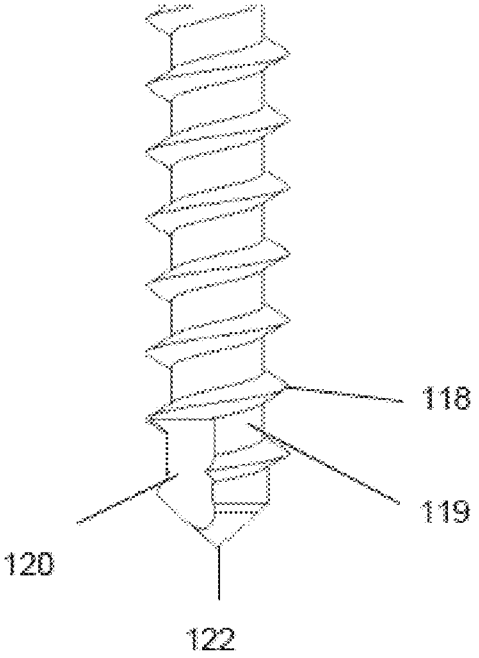
Figure 23(C)

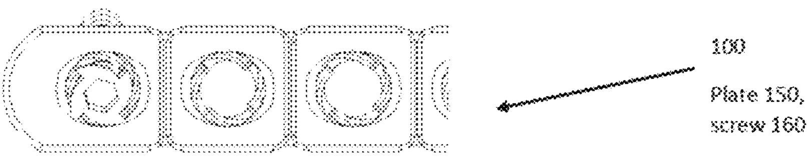
Figure 27(D)
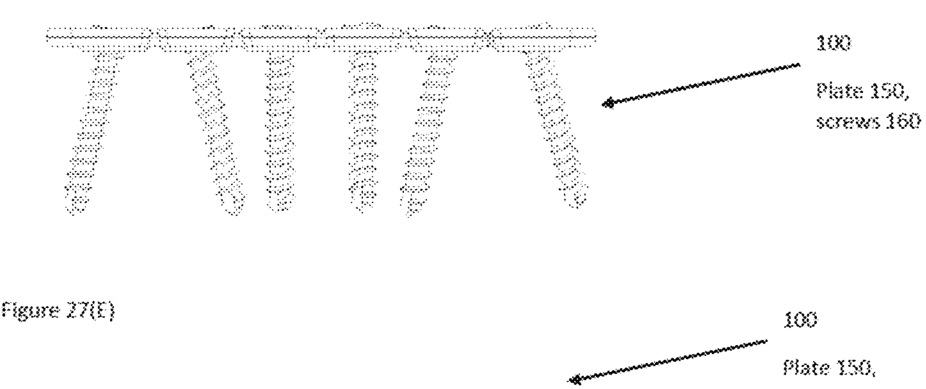
Figure 27(E)
100
Plate 150,
screws 160
Figure 27(F)

BONE FIXATION DEVICE AND SYSTEM AND METHOD FOR USING THE DEVICE

CROSS REFERENCE TO RELATED APPLICATIONS

This application is a U.S. National Stage of International Patent Application No. PCT/EP2021/086656 filed Dec. 17, 2021 which claims priority to U.S. Provisional Application No. 63/126,652 filed Dec. 17, 2020.

TECHNICAL FIELD

The present disclosure relates to a bone fixation device and system and method for using the device. More specifically, the present disclosure relates to orthopaedic surgery, particularly, fracture fixation and corrective bone surgery.

BACKGROUND

Osteoporosis is a bone disease that develops when bone mineral density and bone mass decreases, or when the quality or structure of bone changes. This can lead to a decrease in bone strength that can increase the risk of fractures (broken bones), (National Institutes of Health-Osteoporosis and Related Bone Diseases). It is estimated that there are between 1.5 and 2 million osteoporotic fractures in the United States of America per year (Burge R, Dawson-Hughes B, Solomon D H, Wong J B, King A, Tosteson A. Incidence and economic burden of osteoporosis-related fractures in the United States, 2005-2025. Journal of bone and mineral research. 2007 Mar. 1; 22(3):465-75.). One of the consequences of Osteoporosis is that the fracture fails to heal appropriately and leads to fracture non-union.

Fracture non-union (failure of the bone to heal satisfactorily after a fracture) is reported in between 5-10% of all fracture repairs (Zura R, Xiong Z, Einhorn T, et al. Epidemiology of Fracture Nonunion in 18 Human Bones. JAMA Surg. 2016; 151(11):e162775. doi:10.1001/jamasurg.2016.2775).

There are a number of factors that contribute to the causes of fracture non-union, including location of the affected bone and also patient-related factors and patient conditions, such as insulin/non-insulin dependent diabetes, osteoarthritis+/−rheumatoid arthritis, smoking and obesity, medication, open or closed fractures, high energy trauma and multiple fractures.

The options currently available for fracture fixation include plates and screws, intermedullary nail insertion, joint replacement, temporary wires (K-wires) or external fixation.

There are currently two options for fracture fixation with plates and screws:

- Compression (cortical/nonlocking) where the screw compresses the plate to the bone thus holding the fracture reduced by friction and the fracture heals by primary healing which requires anatomic reduction; and
- Locking screws/plates where the screws are locked to the plate, but the plate is not compressed on the bone which heals by secondary healing (callus formation) which requires micromotion at the fracture site.

Both above-described known plate/screw options can fail due to non-union.

Compression plates can fail, especially in osteoporotic bone, from screw loosening leading to loss of reduction, refracture or non-union. Locked plates can be too rigid to allow micromotion which can result in non-union or failure of the plate. All these potential complications result in a repeated operation causing significant injury to the patient and very high costs to global health service providers.

The global fracture fixation market is expected to reach $12.1 billion by 2025 (Global Fracture Fixation Products Market $12.1 Billion by 2025: iHealthcareAnalyst, Inc.). Plates and screws are expected to account for 40-45% of this very large market. In the USA, EU and other developed economies, populations are becoming older giving rise to increased osteoporosis/osteoarthritis and obesity, which results in a very urgent need to develop new fracture fixation devices.

Numerous devices have been described previously for fracture fixation. For example, International Publication number WO2014057405A1, US 2014/0214036, AU 2011202372 A1, WO2007149325A2.2007-12-27. However, these devices do not provide the surgeon with adequate customisation options to provide an environment that optimises fracture fixation.

The known solution for repair of a non-union is to use hybrid plates which give the option of using either a locked or non-locked screw in one plate screw hole.

SUMMARY

The present disclosure relates to a bone fixation system, device, and a method for using this system and device. The system combines dynamic and compression functions to allow for corrective surgery by bone compression.

The system comprises a bone plate of at least two holes, and associated screws.

The bone plate holes have female locking element which allows for the male locking element on the head of the screw allowing for screw/plate constraint.

The plate has raised elements on the underside of the plate which are the contact points for between the plate and bone.

The areas surrounding screw holes in the top side of the plate are sloped to allow the screws to be placed eccentrically into the bone and allows for compression at the fracture site once contact is made between the screw head and plate.

The indentations on the lateral aspect of the plate and the firebreak trench, located between two screw holes, allow for the bending of the plate in the superior/inferior plane and lateral plane which will provide some degree of intra-operable customisation.

The screws have an indent in the tip allowing for a self-tapping option during insertion. The screws have a right-handed screw thread and the male locking mechanism on the screw head engage with the female component of the plate in a ratchet fashion.

The drawings show, by way of example, only a six-hole plate but of course, it is to be understood that the locking system of the present disclosure can be incorporated into any plate design for any bone of the human/animal body.

The bone plate of the one arrangement according to the specification involves the combination of the two fixation principles (locking and non-locking), however unlike the hybrid plates, where it is an either/or option, the bone plate of the present disclosure provides the option of compression and locking in one screw.

The bone plate of an alternative arrangement include a locking only mechanism.

The bone plate of the present disclosure provides compression in the axial plane (reducing the fracture) and in the perpendicular plane (compressing plate to bone). It can be contourable (i.e. bent to a shape, unlike standard locking plates) and it can prevent periosteal ischaemia (damage) at the fracture site. Periosteal ischaemia is a known contributor to facture non-unions, as the only plate/bone contact happens in a small area surrounding the screw hole allowing for conservation of the bones blood supply between the screw holes.

The bone plate of the present disclosure facilitates the creation of a screw/plate complex, independent of the plate/bone interface.

In one aspect, the present disclosure relates to a locking system comprising a locking bone plate for fracture fixation and a screw, adapted for engagement in the locking bone plate. The locking plate comprises a plurality of screw holes, each screw hole being adapted to receive a screw. The screw of the present disclosure comprises screw threads configured and adapted to allow for insertion of the screw into bone with compression of the plate to bone. The four protruding male components on the screw head allow for the screws to be locked into place in the plate once they interact with the female components of the plate. The screw locking heads are provided in two sizes/dimensions, such that in one version, the screw engages with the locking plate in a plush fit to the locking plate and in the second version, the screw engages with the locking plate in an offset arrangement so as to allow some movement in the screw plate complex i.e. in the locking system of the present disclosure. This allows the surgeon to decide if the fracture needs rigid fixation or some degree of micromotion for optimal healing. On the under surface of the plate, the plate comprises a raised area around the screw hole to allow for preservation of the periosteum of the bone between the adjacent screw holes. The area between adjacent screw holes is malleable to allow for customisation by the surgeon intra-operatively for optimal fracture fixation. The screw head comprises a tapered shoulder to allow for compression at the fracture site if placed in an eccentric position.

In another aspect, the present disclosure also provides a method for bone fixation using the plate and screw system of the present disclosure. The plate and screw assembly system of the present disclosure combines dynamic and compression functions to allow for corrective surgery by bone compression.

The present disclosure provides a plate and screw assembly comprising a bone plate and of at least two holes and associated screws. The bone plate holes comprise protruding female locking element which is adapted to allow for the male locking element on the head of the screw allowing for screw/plate constraint.

The plate of the present disclosure comprises raised elements on the underside of the plate which are the contact points for between the plate and bone.

The areas surrounding screw holes in the top side of the plate are slopped to allow the screws to placed eccentrically into the bone and allows for compression at the fracture site once contact is made between the screw head and plate.

The indentations or channel on the superior and inferior surfaces and on the peripheral of the plate between two screw holes allow for the bending of the plate in the superior/inferior plane and lateral plane which will provide some degree of intra-operable customisation.

The screws of the present disclosure comprise an indent in the tip allowing for a self-tapping option during insertion. They have a right handed screw thread and the male locking mechanism on the screw head is designed to engage with the female components of the plate in a ratchet fashion.

The present disclosure provides the following features:

A locking system for fracture fixation comprising a locking bone plate comprising at least one aperture adapted and configured for receiving a screw that provide a plate and screw complex for fracture fixation.

The locking system wherein the locking plate comprises a plurality of screw holes, each screw hole adapted to receive a screw.

The locking system wherein the screw comprises at least one protruding male element.

The locking system wherein the plate comprising at least one aperture wherein the aperture comprises at least one female element.

The locking system wherein the at least one female element of the aperture is configured to receive the at least one male element on the screw.

The locking system wherein the screw comprises a plurality of screw threads configured for insertion into bone with compression of the plate to bone and the male components on the screw head allow for the screws to be locked into place in the plate once the male components engage with the female components of the plate.

The locking system wherein the screw locking head is configured for plush fit engagement with the locking plate.

The locking system wherein the screw locking head is configured to allow some movement in the screw plate complex.

The locking system wherein on the under surface of the plate, the plate comprises a raised area around the screw hole to allow for preservation of the periosteum of the bone between the adjacent screw holes.

The locking system wherein the area between adjacent screw holes is adapted to allow for customisation by the surgeon intra-operatively for optimal fracture fixation.

The locking system wherein the screw head comprises a tapered shoulder to allow for compression at the fracture site if placed in an eccentric position.

A method of operating the locking system of the present disclosure with the method steps described herein and with reference to the accompanying drawings.

The drawings show a preferred embodiment in which there are six holes in the bone plate but it is to be understood that the locking system of the present disclosure can be incorporated into any plate design for any bone of the human/animal body.

The method may comprise the following steps:

Identify the Fracture/osteotomy/gap in bone;

Retract soft tissue;

Plate is compared to patient's anatomy and adjusted to fit by bending the plate at point equidistant between two adjacent screw hole—using a device similar to a French benders.

If compression at the gap site is desired a drill hole should be made in the bone in an eccentric position (off-centre).

The width of the bone is measured and desired screw length chosen.

The screw is then advanced in a clock-wise (right-handed) direction.

The shoulder of the screw head will contact the slope of the plate and as it advances further it will move the plate longitudinally (and therefore close the gap in the bone) to allow it to be in a centric position.

The screw is over tightened to the desired tension by the surgeon, a torque limited maybe incorporated into the screwdriver preventing over tightening.

The screw is advanced and the male components of the screw head engage with the female components of the plate. The male components will interact with the female components and lock into place.

In an optional step, relating to the method, should a screw need to be removed—axial pressure should be applied to disengage the locking mechanism and the screw is turned clock-wise (right hand direction) for a quarter turn to allow clearance of the screw for the locking complex. It is then twisted anti-clockwise (left hand direction) until out of the bone. A custom fit screwdriver sleave is advanced over the screw once all the male components have disengaged and this sleave will prevent the male screw components from re-engaging with the female components and allow for removal of the screw.

Benefits and advantages of the present disclosure include the following. Patients have a decreased risk of non-union/failure and need thus need for re-operation. Also, the patient healing time is decreased, which evidently results in a quicker return to normal daily activities, i.e. work.

According to a further aspect the specification provides a bone plate of a bone fixation system configured to provide a combination of dynamic and compression functions to allow for corrective surgery by bone compression the bone plate having an upper external surface and a lower bone facing surface and at least two screw holes, for receiving associated screws;

- the bone plate screw holes comprising female engagement elements which are configured to interact with corresponding male engagement elements on a head of the screw to provide screw to plate constraint;
- the bone plate comprising more recessed areas surrounding the screw holes in the top side of the plate, wherein the recessed areas are sloped and configured to allow the screws (160) to be placed eccentrically into the bone and allow for compression at the fracture site once contact is made between the screw head and plate.

The recessed areas may be sloped and configured to allow the screws to be placed eccentrically into the bone and allow for compression at the fracture site once contact is made between the screw head and plate.

According to a further aspect bone plate of a bone fixation system configured to provide a combination of dynamic and compression functions to allow for corrective surgery by bone compression the bone plate having an upper external surface and a lower bone facing surface and at least two screw holes, for receiving associated screws;

- the bone plate comprising one or more protrusions protruding relative to the lower bone facing surface of the plate, the protrusions having a surface defining the bone to plate interface; wherein the protrusions of the plate define a bone to plate contact surface having an area less than the area of the lower bone facing surface.

The protrusions may be located around the screw holes. The protrusions may have an annular or ring shaped form.

The specification further provides a bone fixation system configured to provide a combination of dynamic and compression functions to allow for corrective surgery by bone compression, the system comprising:

- a bone plate having an upper external surface and a lower bone facing surface and at least two screw holes, and associated screws;
- the bone plate and screws comprising corresponding engagement elements to provide screw to plate constraint, the bone plate screw holes comprising female engagement elements which are configured to interact with corresponding male engagement elements on a head of the screw to provide screw to plate constraint;
- the bone plate further comprising recesses located between two adjacent screw holes, the recesses configured to allow for the bending of the plate to provide for intra-operable customisation of the form of the plate to a bone of a patient.

The device of the present disclosure is very user friendly which is of benefit to medical staff.

As the failure rates of the device decrease the need for re-operation on the patient, hospital/health care admission rates are decreased, which evidently decreases hospital/health care bed usage.

The benefits of the present disclosure extend to medical insurers and/or payers, as the cost spent on inpatient stay is decreased.

The plate and screw assembly of the present disclosure enables the combining of the two fixation principles (locking/non-locking types of fixation) but unlike the hybrid plates of the prior art where locking/non-locking is an either/or option, the plate and screw assembly of the present disclosure provides the option of compression and locking in one screw. The plate of the present disclosure allow compression in the axial plane (reducing the fracture) and in the perpendicular plane (compressing plate to bone). It can be contourable (i.e. bent to a shape, unlike locking plates) and it can prevent periosteal ischaemia (damage) at the fracture site, a known contributor to fracture non-unions as the only plate/bone contact happens in a small area surrounding the screw hole allowing for conservation of the bones blood supply between the screw holes.

The locking system comprising the plate and screw of the present disclosure facilitates the creation of a screw/plate complex independent of the plate/bone interface.

Additional features and advantages of the present disclosure are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations.

FIG. 4 shows the superior surface of the screw head;

FIG. 9 shows a lateral cross-sectional view of a screw hole of the plate, including a magnified view of one of the four female components of the locking mechanism which will form the main constraint i.e. limit of travel for the screw once it is engaged with the male components of the screw head;

FIGS. 10-19 are CAD drawings of the locking system comprising the bone plate and screw of the present disclosure, showing features of the bone plate and screw assembly and the steps of engagement of the screw head in the apertures of the plate of the present disclosure;

FIG. 11 is a superior view of the screw head locked into the plate;

FIGS. 12 and 13 are lateral view of the screw head locked into the plate;

FIG. 14 is a superior view of the screw head locked into the plate;

FIG. 15 is a superior view of the screw head placed in the eccentric position in grayscale prior to the insertion position as shown in FIG. 14;

FIG. 16 is a lateral view of the screw head placed in the eccentric position in grayscale prior to the insertion position as shown in FIG. 14;

FIG. 17 is a magnified superior oblique views of the screw locked into the plate;

FIG. 18 is a superior oblique views of the screw locked into the plate;

FIG. 19 is a superior oblique view of the screw in the eccentric position relative to the plate prior to engagement (step prior to FIGS. 17 and 18);

FIGS. 22(A), 22(B), 22(C) and 22 (D) provide a perspective view, plan view from above, plan view from the side and a further perspective view respectively of a screw 160 according to an exemplary arrangement of the specification; the screw 160 is formed to have corresponding features to those of the screw hole of plate 150, of FIGS. 20 and 21, and configured to interact with the plate 150;

FIGS. 23(A), 23(B) and 23(C) provide perspective view from different sides of tip of screw 160 of FIG. 22;

DETAILED DESCRIPTION

The present disclosure relates to a bone fixation device, and a system and a method for using this device. The device combines dynamic and compression functions to allow for corrective surgery by bone compression.

Figure 1:
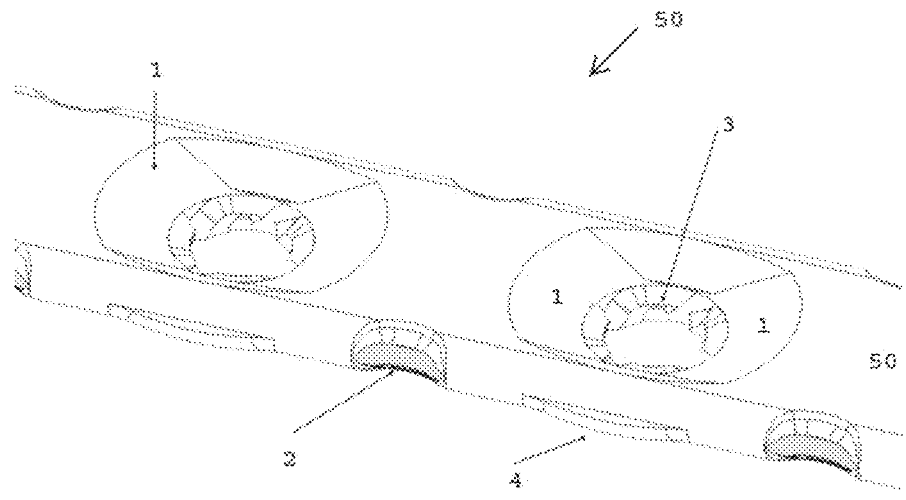
FIG. 1 is an elevated view of a portion of the plate in a first embodiment.

Now referring to the figures, initially to FIG. 1, there is shown an elevated view of the plate 50 of bone fixation system 500 of FIGS. 1 to 19. There is a sloped face 1 in the longitudinal axis from the screw hole to the superior surface of the plate 50, this provides a point for interaction with the shoulder of the screw head allowing for the plate to be moved longitudinally as the screw is compressed against the plate. This will result in compression at the fracture/osteotomy site. Now referring to the figures, initially to FIG. 1, there is shown an elevated view of the plate 50. There is a sloped surface 1 in the longitudinal axis from the screw hole to the superior surface of the plate, this provides a point for interaction with the shoulder of the screw head allowing for the plate to be moved longitudinally as the screw is compressed against the plate. This will result in compression at the fracture/osteotomy site. Equidistant between each screw hole is an indentation, preferably, in the form of a semi-spherical cut out 2 of the plate and this will be the fulcrum of the bending forces between adjacent screw holes when the plate is adapted intra-operatively to match the patient's anatomy. The cut-out 2 is also referred to as recess 2. In the screw hole of the plate there are four female components of the locking mechanism 3. The overhang/tooth of the female component will contain the screw head by interacting with one of the male components of the screw head preventing backing out of the screw. The female components are designed with a degree of offset so that they can contain the plush fit screw head or the offset screw head if the surgeon desires a small amount of micromotion between the screw and plate interface to optimise the environment for bone healing. On the underside of the plate, there is a protrusion from around the screw hole (the circular protrusions are indicated by reference numeral 5 in FIG. 3) and these protrusions will define the plate bone interface. In a preferred embodiment, the protrusions comprise a smooth surface and may preferably, comprise 0.5 mm circular smooth surfaces. In one alternative embodiment (alternative version of the plate), the plate bone interface may comprise a roughened surface to allow for osteogenesis of the bone onto the plate for increased stability if deemed necessary by the surgeon.

Figure 2:
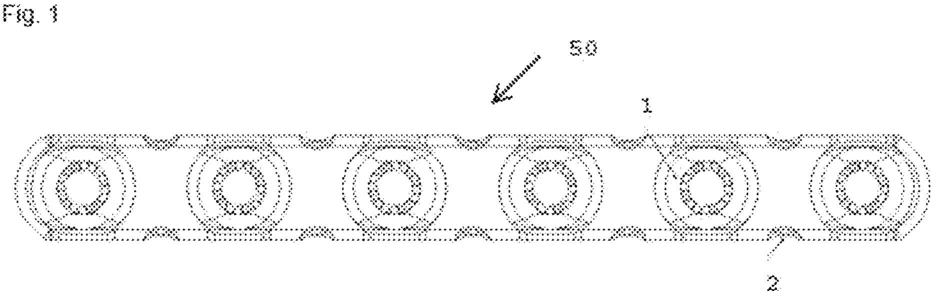
FIG. 2 is a plan view from above (superior view) of the bone plate in the first embodiment.

Referring now to FIG. 2, there is shown one embodiment of the plate comprising a plurality of holes arranged in the same plane, in a linear configuration along the longitudinal axis of the plate; in this particular embodiment, the plate comprises 6 holes but of course, this number can be varied and falls within the scope of the present disclosure. In this embodiment, the plate comprises a sloped surface surrounding the screw hole (1) and the plate also comprises a spherical cut out between each screw hole (2) thereby providing a plurality of spherical cut-outs provided in the plate.

It is to be understood that other versions of the plate will be available depending on the anatomic site of the fracture/osteotomy.

Figure 3:
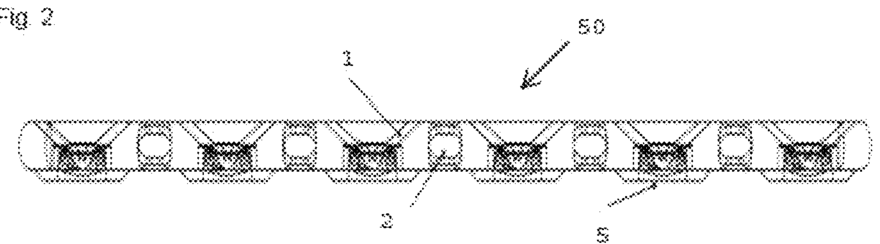
FIG. 3 is a lateral (side) view of the plate in the first embodiment.

FIG. 3 shows a side view of the plate in the first embodiment. The protrusions on the underside of the plate (5) are shown in more detail in this view. The islands between each protrusion defines the site of bending in the superior inferior plane to allow for anatomic customisation of the plate to accommodate a particular patient's anatomy.

Figure 4:
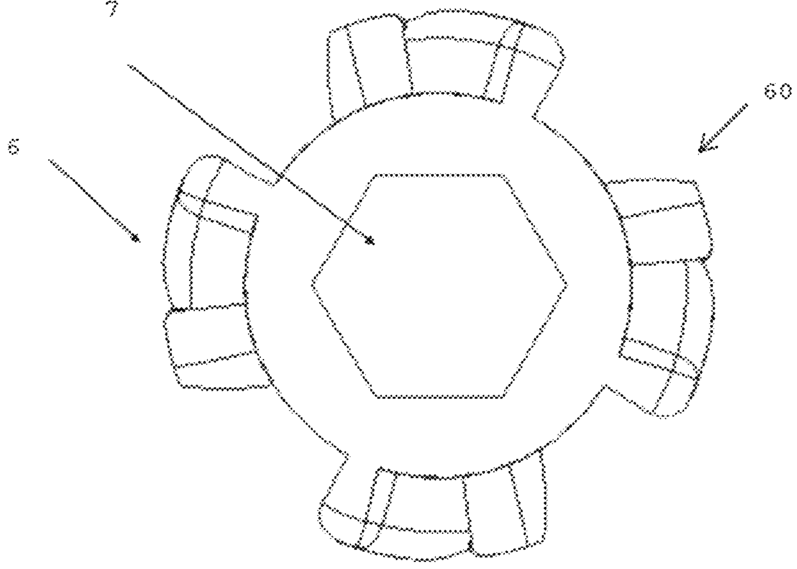
FIG. 4 is a superior view of a screw for engaging with the plate of the first embodiment.

FIG. 4 is a superior view of a screw showing the superior surface of the screw head. The screw head includes a standard hexagonal indentation (7) allowing for insertion of a standard hexagonal screwdriver head to allow for rotational force to be applied to the screw. The four male projections (6) are seen here projecting circumferentially from the screw head. These interact with the female components of the plate facilitating the locking the mechanism.

Figure 5:
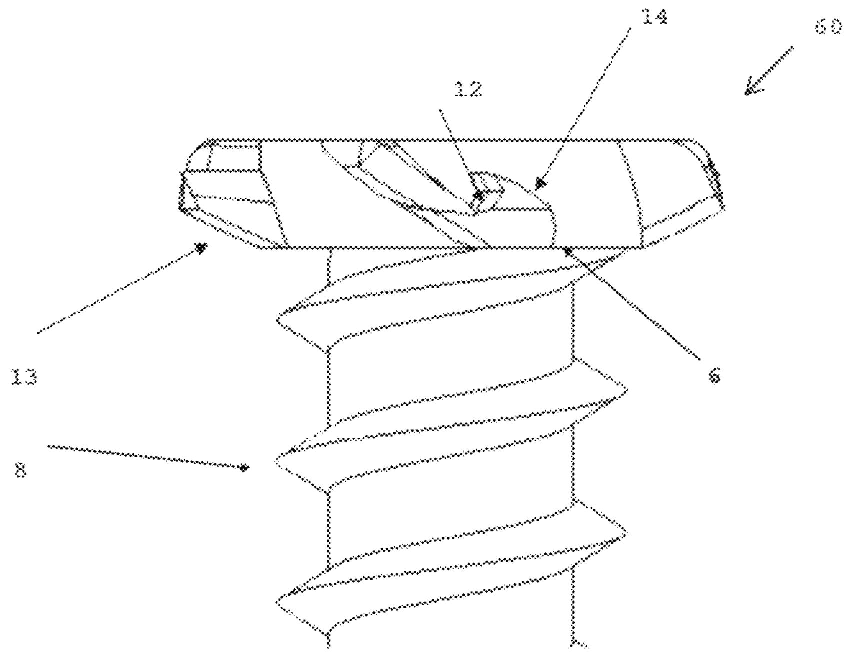
FIG. 5 is a lateral view of the screw comprising the screw head and the proximal threads of the screw.

FIG. 5 illustrates a lateral view of the screw head and the proximal threads. The under surfaces (shoulder of the screw head) of the male projections (13) are chamfered to so as to interact with the sloped surface of the plate. This allows for axial pressure applied by the screw to the plate to be changed to longitudinal movement of the plate and thereby reducing the gap in the bone (fracture/osteotomy) and compressing the space optimising osteosynthesis. The anterior surface of the male projections (14) are angled to be one quarter of the screw thread (8) pitch so that when the screw is over tightened by a quarter turn in the right hand direction and then turned in the left hand direction the male projection will engage with the female components of the plate and minimal compression of the plate on to the bone will be lost. The under surface of the screw head is also seen here (6). There is an area in the male projection (12) that allows for the engagement of the female component of the plate. This area will come in two different sizes (plush fit and offset) depending on the screw type the surgeon wishes to use. this will provide the surgeon with the option of absolute stability or some relative motion in the screw and plate complex.

Figure 6:
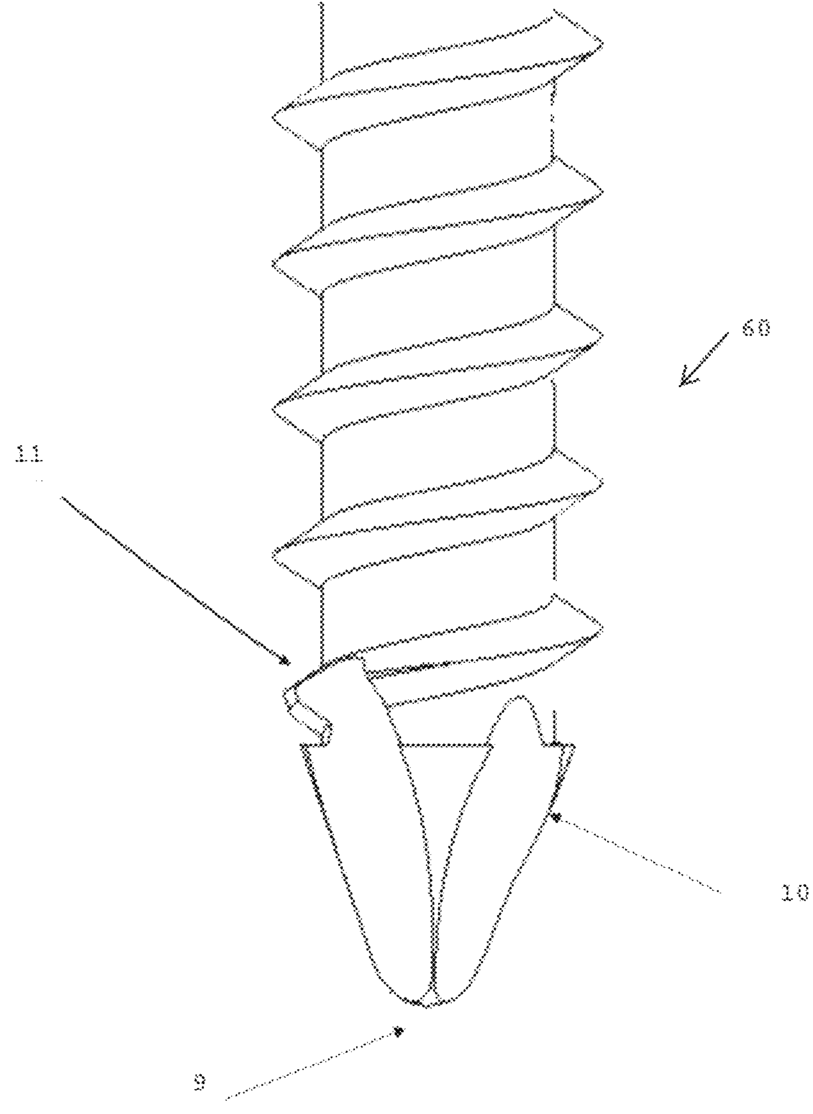
FIG. 6 is an exploded view of screw of FIG. 5.

Referring now to FIG. 6, which is an exploded view of the screw of FIG. 5, the lateral view of the distal portion of the screw and tip of the screw are shown. The screw comprises a tip (9) and the cutting edge (10) of the screw tip (9). The superior area of the screw tip (11) allows for bone debris to be projected up the screw so that the bone debris does not interfere with the fixation of the screw to the bone.

Figures 7A, 7B, 7C:
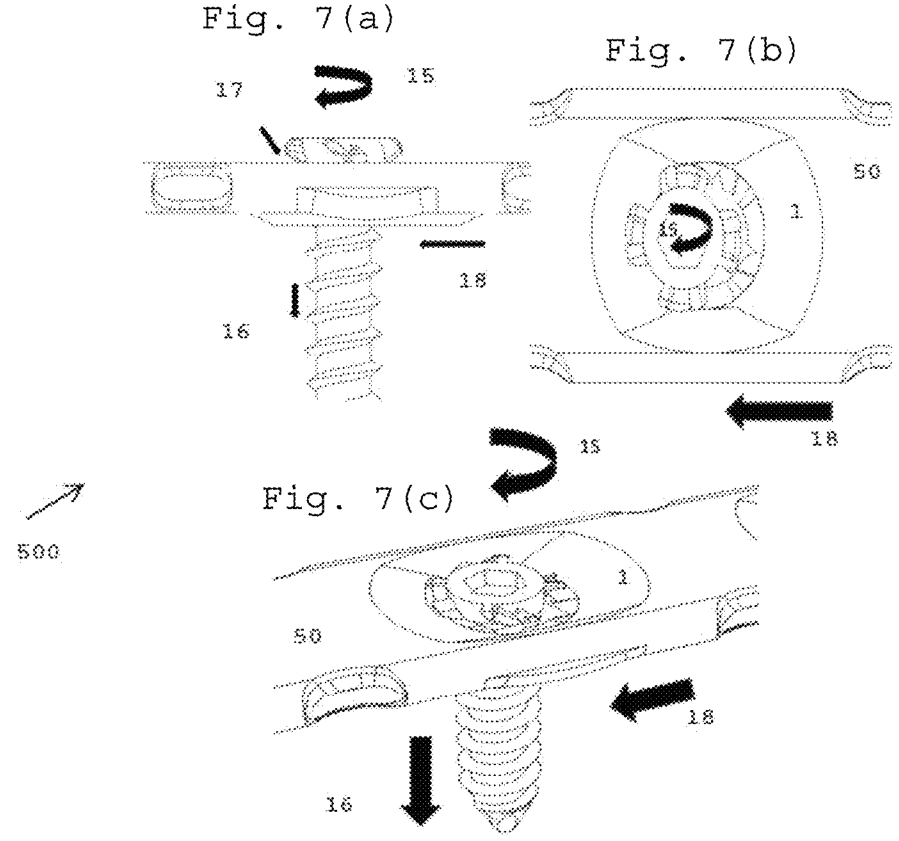
FIGS. 7 (*a*) (*b*) and (*c*) show the lateral, superior and oblique views of the plate screw assembly in the process of engagement of the screw with the plate.

FIGS. 7 (*a*) (*b*) and (*c*) show the lateral, superior and oblique views of the locking system comprising the plate screw assembly, in the process of engagement of the screw with the plate. The screw is inserted into the bone in a clock-wise (right handed direction indicated by the arrow 15) and is in n eccentric (off-centre) position in relation the screw hole in the plate. As the screw advances (16), the shoulder of the screw head contacts the inwardly sloped surface of the plate (17) thereby forcing the plate to move longitudinally (18) to allow the screw to become centric in the screw hole of the plate. The screw is overtightened by a quarter turn.

Figures 8A, 8B, 8C:
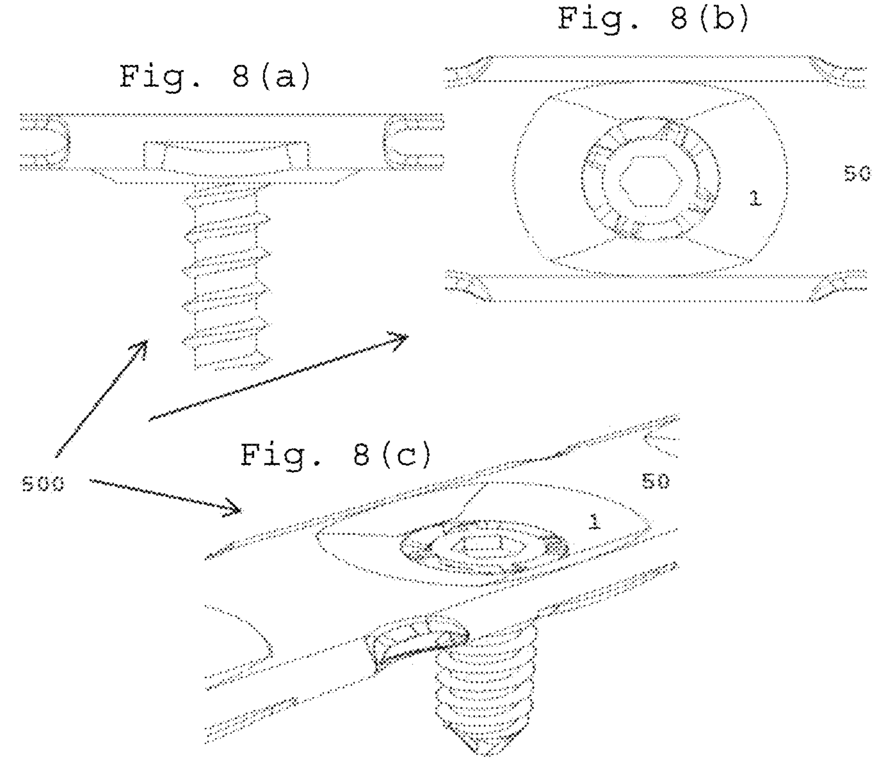
FIGS. 8 (*a*) (*b*) and (*c*) show the steps of the method for locking the screw in the screw hole; with FIG. 8(*c*) showing the final step in which the screw is locked in screw hole of the plate.
Figure 8:
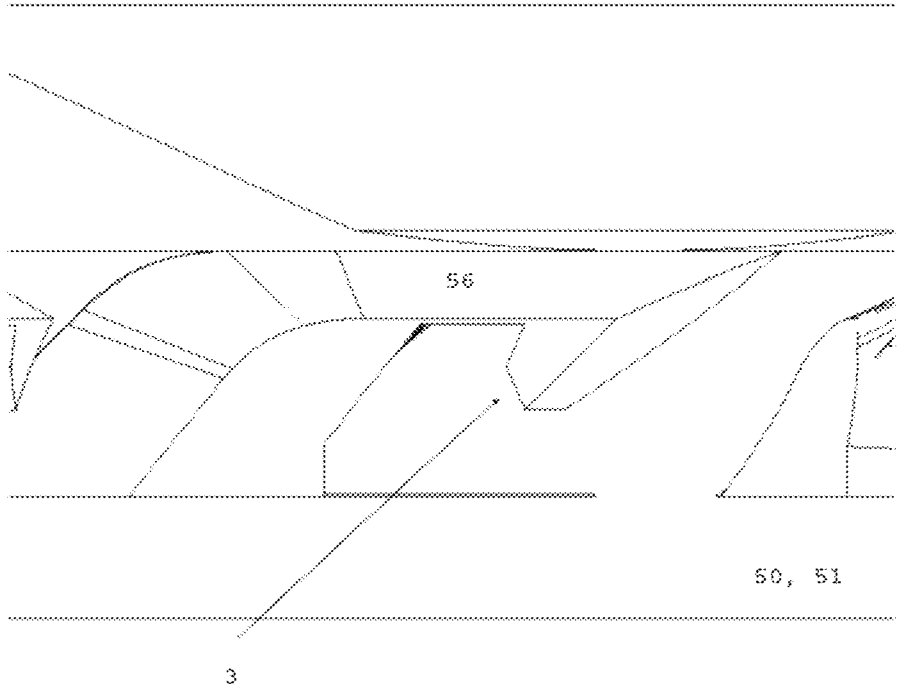
Figure 10:
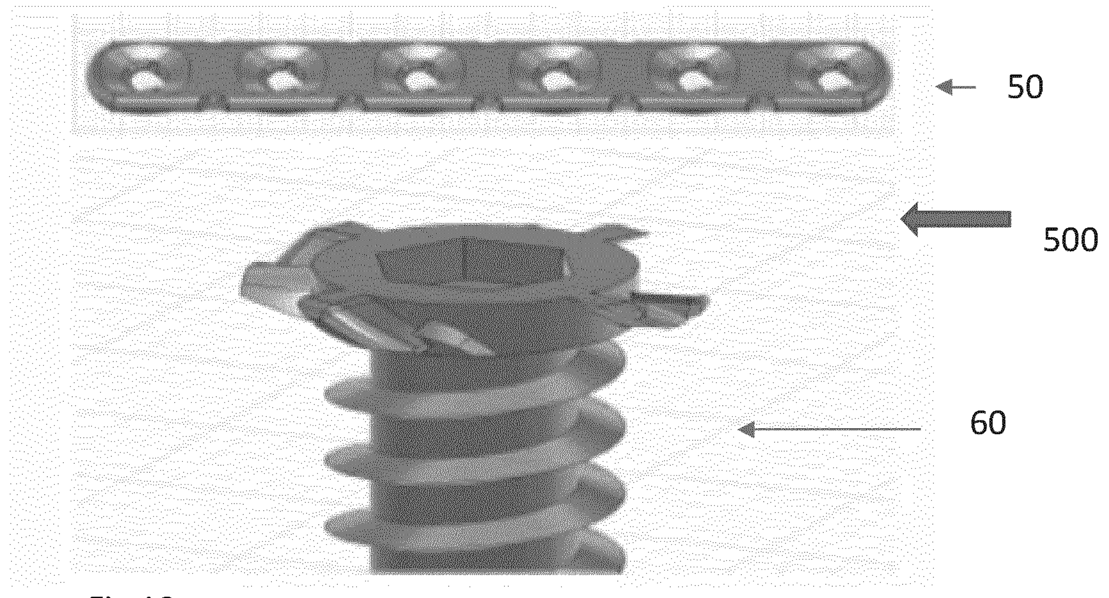
Figure 11:
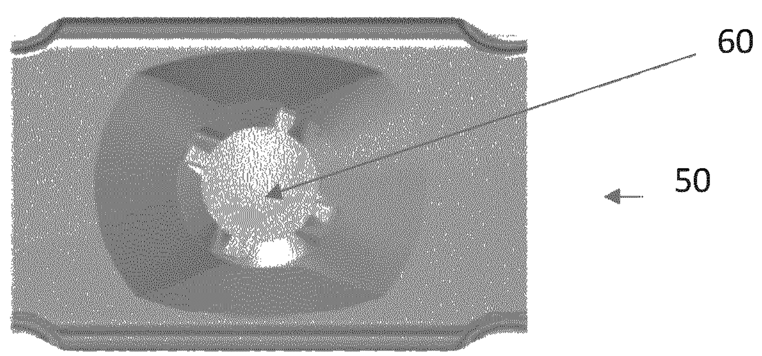
Figure 12:
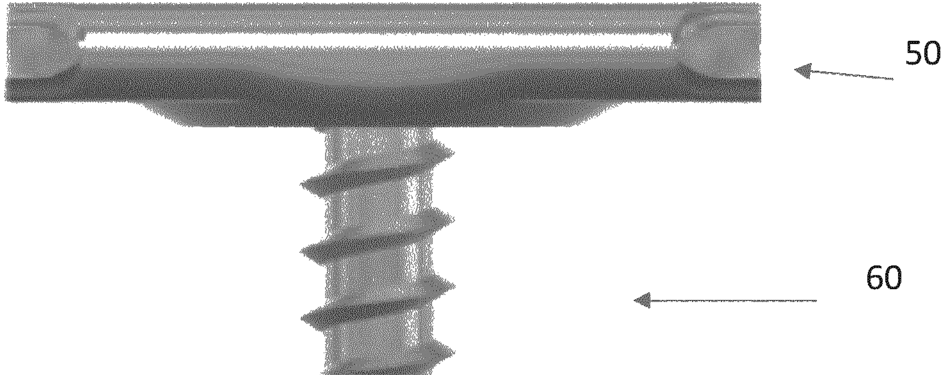

FIGS. 8 (*a*), (*b*) and (*c*) show the lateral, superior and oblique views of the plate screw assembly after the screw is turned anti-clockwise (left hand direction) by a quarter turn. This enables the male and female components of the screw/plate complex to engage and lock in-situ without much loss of compression of the plate onto the bone.

Referring now to FIG. 9, there is shown a lateral cross-sectional view of a screw hole of the plate. A magnified view of one of the four female components of the locking mechanism which defines the limit of travel for the screw once it is engaged with the male components of the screw head.

FIGS. 10 to 19 illustrate CAD drawings of the bone plate and screw of the present disclosure.

Referring to FIGS. 20 to 27, further alternative arrangements of a system 100 comprising a bone plate 150 and screws 160 according to the specification are described.

Figures 20A, 20B:
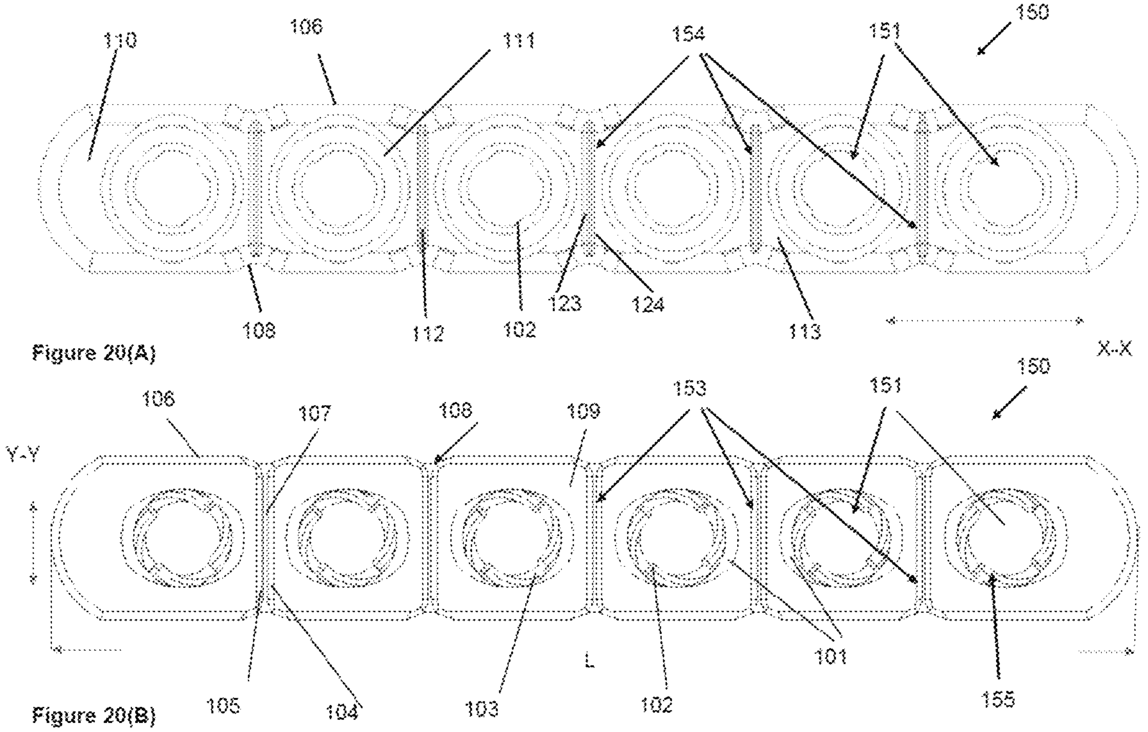
FIGS. 20(A), 20(B) and 20 (C) provide respectively a plan view from below, a plan view from above and side plan view of a plate 150 according to a further exemplary arrangement of the specification.
Figure 20C:
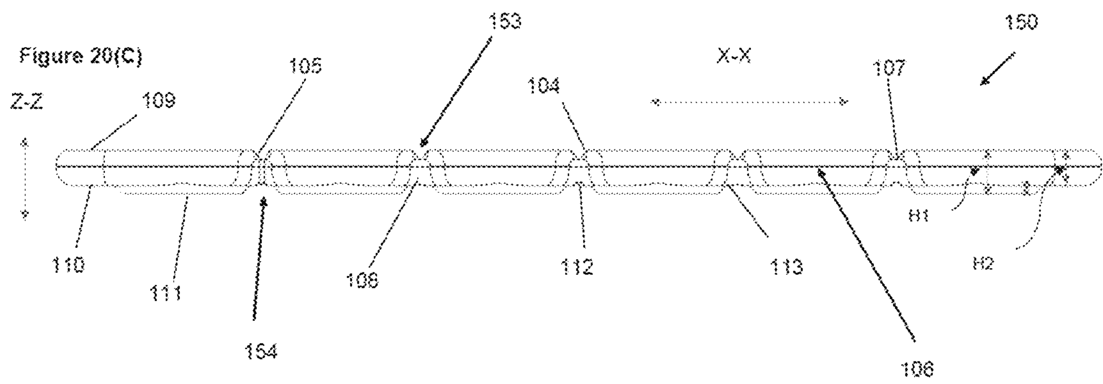
Figures 21A, 21B:
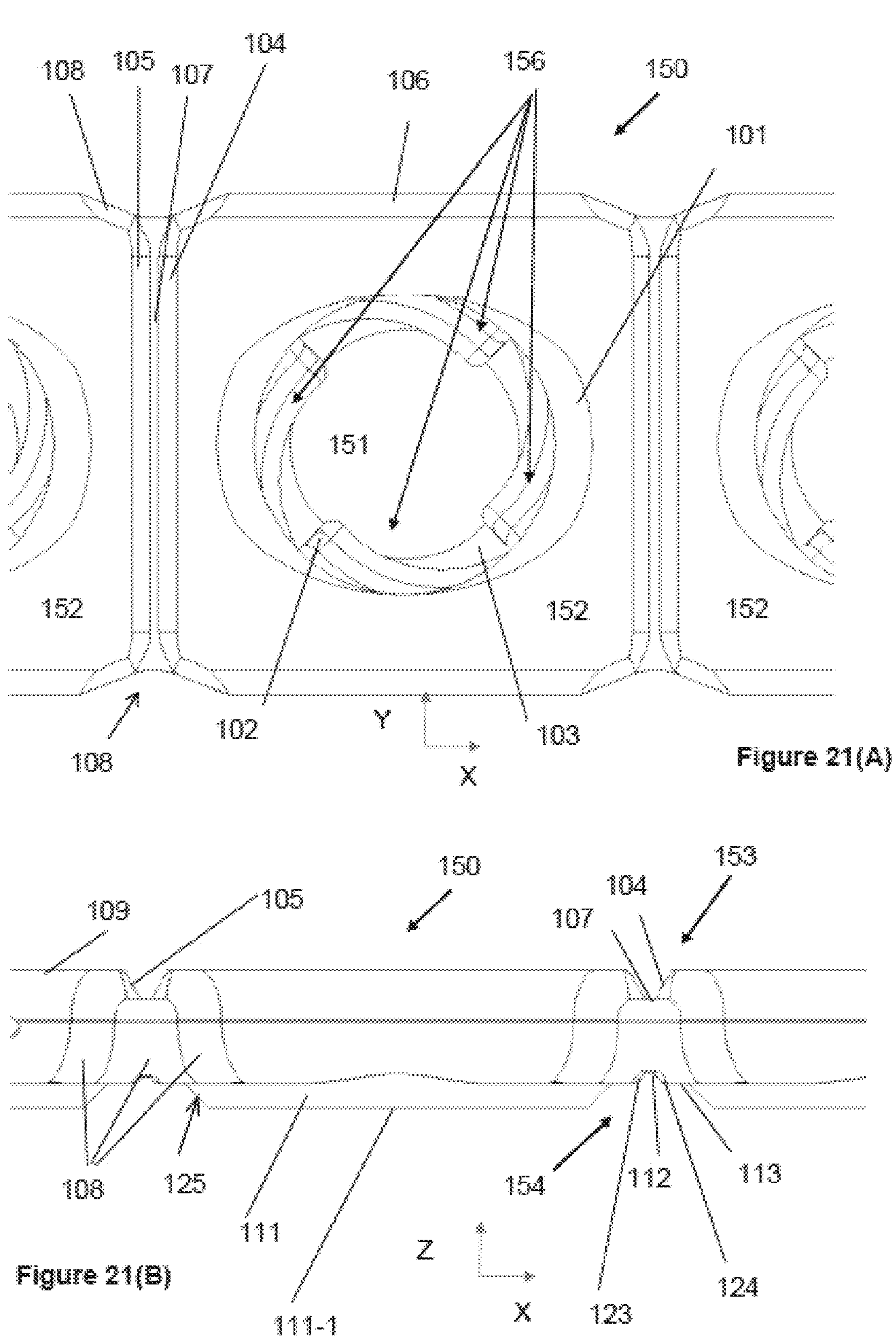
FIGS. 21(A), 21(B) and 21 (C) provide respectively a plan view from above, a side plan view and a perspective of a section 152 of plate 150 of FIG. 20 showing details of the screw hole, screw hole locking mechanism features and channels of the plate 150.
Figure 21C:
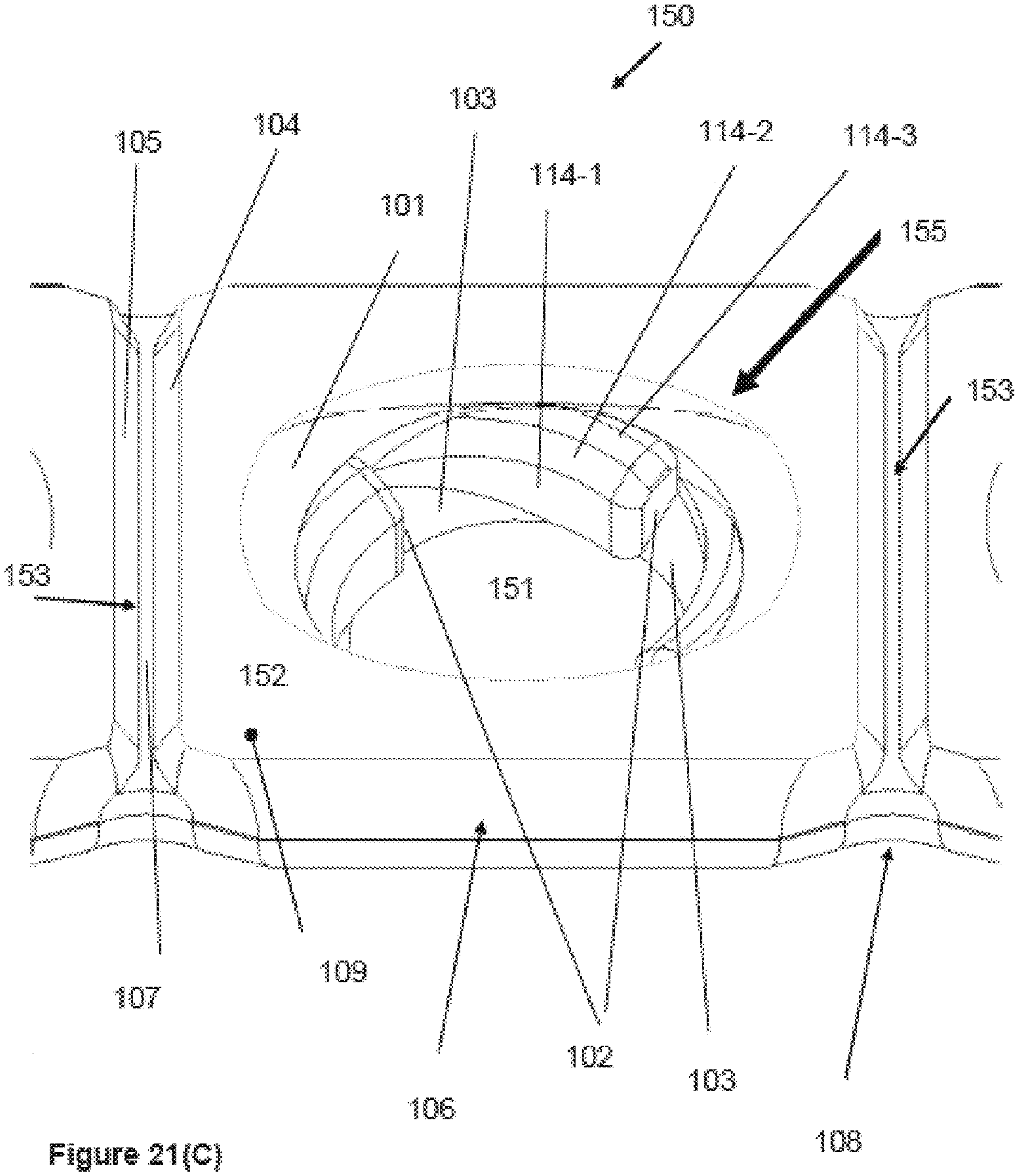

Referring to FIGS. 20 and 21, bone plate 150 of an exemplary arrangement is described. In the arrangement of FIGS. 20, the exemplary bone plate 150 comprises six screw holes 151 and six sections 152. Each screw hole 151 comprises a locking mechanism 155 configured for engagement or for fixing with a corresponding locking mechanism 165 of screw head 161 of screw 160. The screw head 160 is insertable into the screw hole to engage features of the screw head 161 with the screw hole 151. The screw head 161 and the screw hole comprise inter-engaging features. The screw head 161 and screw hole 151 comprise conforming features to allow the inter-engagement. The fixing mechanisms 155, 165 are configured such that they may be used to provide a locking engagement between the screw and plate.

In effect the system 100 of the present specification provides by virtue of the combination of features of the screw and plate the options of compression and locking by the use of a common type or single type screw 160 in combination with the plate 150. The arrangement provides improved flexibility for the surgeon as the screws 160 are interacted with the screw holes 151 of the bone plate 150. The combination of features and the locking technique allows for a lower profile plate, increased customisation of the plate, including during surgery and enhanced healing ability of the bone fracture.

The bone plate 150 comprises a superior (upper surface) 109 and an inferior (lower surface) 110. The lower surface 110 is the bone facing surface, in use. The upper surface 109 is the external surface, in use. The plate 150 comprises side walls defining side edge surfaces 106 of the plate. The edge surfaces 106 may be rounded or sloped.

The bone plate 150 of the exemplary arrangement has a length L in the longitudinal (X-X) axis direction and width W in the lateral (Y-Y) axis direction and a height H in the vertical (Z-Z) axis direction. The upper external and lower bone facing surfaces 109, 110 define transverse planes (the surfaces are arranged in X-Y) of the plate. The plate comprises longitudinal side edge surfaces 106. The longitudinal edge surfaces are arranged in a generally vertical plane (X-Z) of the plate. However, it will be appreciated that other suitable arrangements of the edge surfaces may provided, for example, the edge surfaces may be arranged at a slope or may be rounded. The screw holes 151 comprise a generally cylindrical form and the central axis of a screw hole(s) is a vertical axis in the Z-Z direction running from a top surface to a lower surface relative to the surface of the plate. Features of a screw holes are arranged circumferentially about the central axis (Z) axis thereof.

The locking mechanism 155 of the screw hole 151 comprises a top surface recess 101. Recess 101 comprises a sloped surface or a chamfered surface. The surface of the recess 101 is arranged to slope outwardly at an angle from the screw hole 151 to the upper surface 109 of the plate. The recess 101 is configured for interaction with shoulder features 116 of the screw head 161. The screw hole 151 is recessed relative to the surface 109.

The recess 101 comprising the sloped surface is configured to allow the screws 160 to be placed eccentrically into the bone and allow for compression at the fracture site once contact is made between the screw head and plate.

This interaction between features of the screw and the recess 101 provides the ability to compress (reduce) the fracture if the drill hole for introduction of the screw is drilled in an eccentric position so that once the shoulder of the screw head 116 interacts with the chamfer of the screw hole 101 the pressure applied by the screw head forces the plate either distally or proximally (in the X-X axis) thus closing the fracture gap.

The recesses 101 are configured such that the screws 160 are insertable at an angle of up to but not limited to 20 degrees relative to a plane perpendicular to the plate in any direction allowing the surgeon to create the optimum plate bone construct.

The screw hole 151 and screw head 161 are configured such that interactions between features of the respective fixing mechanisms 165, 155 of the screw head and screw hole allow for the plate 150 to be moved longitudinally as the screw 160 is compressed against the plate 150. As the screw advances, the shoulder of the screw head 116 contacts the inwardly sloped surface of the plate 101 thereby forcing the plate to move longitudinally (in the direction of the longitudinal axis (X-X) of the plate) to allow the screw to become centric in the screw hole of the plate.

The plate and screw are configured such that interaction of the screw head features 115 with the screw hole features 102 provides for a controllable compression at the fracture site or the osteotomy site. As the screw 160 is advanced once it is centric in the screw hole 151, it effectively pushes the plate 150 against the bone, thus compressing the plate to the bone.

In the plate 150 of the exemplary arrangement, the fixing mechanism 155 (also referred to as the locking mechanism 155) of screw hole 151 comprises four female engagement components 156. Each female engagement component 156 including a surface 102, recess 103, and wings 114. The female engagement components 156 are arranged circumferentially around the screw hole (central axis) as illustrated in the exemplary arrangement of FIGS. 20 and 21. The engagement components 156 and the engagement surfaces 102 are equally spaced apart around the screw hole 151. The radius of the screw hole is greatest at the recess 103 and least at the inner edge of the surface 102.

The female engagement surface 102 is configured to contact a male engagement surface 115 of the screw head 161. As the screw is advanced the male engagement surface may be moved into contact with the female engagement surface. By contacting surfaces 102 and 115 may be locked together to prevent toggling or backing out of the screw 160. The surfaces 102 and 115 may be locked in a ratchet manner. The engagement surface 102 is configured to act as a stop to corresponding male engagement feature 115 of the screw head 161. When in the locked position, the male engagement feature abuts the female engagement feature.

Recess 103 is provided adjacent the engagement surface 102. The recess 103 is configured to accommodate a corresponding feature of the male component of the screw head 161. The recess 103 defines a receiver for receiving a portion of the male engagement feature of the screw head. The recess 103 is the tapered end of the female component 156 of the plate and allows for the tapered end of the male component of the screw to settle. This constraint enables the continued compressive element of the screw onto the plate and thus onto the bone.

Each female engagement component 156 of the screw hole locking mechanism 155 comprises engagement surface 102 and recess 103. Each female engagement component 156 further comprises a wing 114 arranged between the engagement surface 102 and recess 103. The wing 114 comprises a chamfered surface 114 which conforms to a shoulder 116 of the male engagement feature of the screw head 161. The wing 114 in the exemplary arrangement comprises a tapered side wall 114-1 and sloping top wall 114-3, 114-2. The wing 114 and therein the walls of the wing are tapered from the engagement surface 102 to the recess 103.

In the exemplary arrangement of FIGS. 18, the tapered side wall 114-2 tapers from the widest and highest extent thereof starting at a first engagement surface 102 to define a recess 103 adjacent the next engagement surface 102. The recess 103 is provided between the tapered end of wing 114 and the adjacent surface 102. The sloping top wall 114, 114-2 similarly tapers in height (Z axis of the plate) and width (relative to the vertical axis of the screw hole) from the first engagement surface 102 to the recess 103.

The female engagement components 156 each having an engagement face 102, recess 103 and the wings 114 are arranged generally circumferentially to the screw hole. The female engagement components 152 of the fixing mechanism correspond to those of the male engagement features of the screw head.

In the arrangement of FIGS. 20 and 21 the screw hole 151 comprises four female engagement components 156 of the locking mechanism 155. Four recesses or receivers 103 are provided in the screw hole adjacent the engagement surfaces 102. Four wings 114 are provided between the engagement surfaces and recesses. It will be appreciated that the screw hole may be provided with a different number of female engagement components 156. According to a preferred arrangement of the specification the screw hole 151 comprises at least two female engagement components 156. The screw head 161 comprises a corresponding number of male engagement components 166 to that provided to the screw hole 151. In the exemplary arrangement of system 100 of FIGS. 20 to 26 four of each of the female and male engagement components are provided. The arrangement including four female/male engagement features is advantageous as it provides for adequately securing and locking the screw in the screw hole of the plate but not require over tightening/compression of the plate to the bone. Locking to a selected locking position can be achieved also with a quarter rotation of the screw head.

The screw and screw hole are arranged in locking engagement when the male components 115, 116 of the screw engage with the plate and are continually rotated/advanced until the optimal compression of the plate against the bone is achieved, Once the surgeon is content with the compression the screwdriver is removed allowing for the surfaces 115 and 102 to contact or abut each other and surface 102 prevents surface 115 from toggling/backing out.

An alternative screw head configuration provides a degree of offset of surface 115 with respect to plate surface 102 so that they can contain a plush fit screw head 161 or an offset screw head 161. The different types of screw head e.g. plush fit or offset are provided for use for example in the event that the surgeon desires a small amount of micromotion between the screw and plate interface to optimise the environment for bone healing.

The bone plate 150 of the arrangement of FIGS. 20 and 21 comprises a plurality of sections 152 arranged side by side along the longitudinal axis (X-X) of the plate. The bone plate 150 comprises a plurality of channel or trough features 153, 154 which define sections 152 of the plate 150.

Channel feature 153 also referred to as a trough feature 153 or trench feature 153 is provided on the upper surface 109 between each section 152. The channel feature 153 is arranged transversely across the upper surface of the plate between the first and second side edges.

The channel feature 153 is arranged in the direction of the lateral (Y) axis of the plate. Channel feature 153 on the upper surface 109 (external surface in use) of the exemplary arrangement of FIG. 18 comprises a generally concave form relative to the surface 109 of the plate 150. The channel 153 may comprise for example a generally semi-circular or V-shaped or truncated V shaped form or U-shaped form in cross section (when plate is oriented top external surface up/lower bone facing surface 110 down). The channel feature comprises a base 107 and side walls 104 and 105. The side walls are arranged to slope outwardly from the base 107 to the upper surface 109. The channel feature 153 is arranged across the width of the plate from a first side wall 106 to the second side wall 106. The channel 153 runs in the lateral direction essentially in the direction of the Y axis of the plate.

The lower or bone facing surface 110 of the plate 150 further comprises channels 154 recessed relative to the lower surface 110. Channels 154 are of generally convex form or inverted V-shaped or U-shaped form relative to the lower bone facing surface 110 (when plate is oriented top external surface 109 up/lower bone facing surface 110 down). Channel features 154 are arranged transversely across the lower bone facing surface 110 of the plate between the first and second side edges. The channel feature 154 is arranged in the direction of the lateral (Y) axis of the plate. The channels 154 on the lower side comprise an apex or top portion 112, and side walls 123 and 124 sloping from the apex of the channel to a surface portion 113 of lower side surface 113.

Each channel 153, 154 provides in effect an indentation relative to the respective surface of the plate. Channels 153 and 154 are provided located between adjacent screw holes 151 Channels 153 and 154 are provided located midway between the screw holes 152. Screw holes 151 are centrally located in sections 152. The channels and screw holes are equally spaced apart along the longitudinal axis of the plate of the exemplary arrangement of FIG. 18. The channels 153 and 154 are arranged back to back on the opposing upper and lower surfaces of the plate.

Upper side channels 153 the lower side channels 154 are configured to act as the fulcrum of bending forces between adjacent screw holes when the plate is adapted intra-operatively to match the patient's anatomy. The arrangement of the channels 153 and 154 is configured in particular to allow bending of the plate 150 about the channels 153, 154.

In particular, the channels 153, 154 are configured to allowing bending or movement of a first section 152-1 of the plate relative to an adjacent second section 152-2.

Channels 153, 154 have a channel axis. The sections on either side of the channel may be rotated relative to one another about the channel axis by virtue of the configuration. In the drawings the channel axis is arranged in the direction of the lateral axis (Y-Y) of the plate. A first section 152-1 may be moved or rotated about the central axis of the channel 153 or channel 154 to change the orientation of the surfaces 109-1, 110-1 of a first section 152-1 relative to that of the surfaces 109-2, 110-2 of a second adjacent section 152-2. In effect the pitch of the transverse surface—surface 109 of section 152-1 (i.e. X-Y plane defined by section 152-1) may be adjusted about the axis of channel 153 or channel 154. The angle of the transverse surface of the section 152-1 to the horizonal is adjustable.

The channels 153, 154 are configured to allow for bending of the plate 150 about the channel. By virtue of the features of the plate, the plate is configured to allow the surgeon to arrange the surface 109 or transverse plane of a first section 152 at a different angle relative to the surface 109 of a second adjacent section 152 of the plate. The first section 152 of the plate may be moved about the channel 153 relative to the second adjacent section of the plate. The movement of the first section about the channel relative to the second section results in a change of the angle or pitch of the transverse plane (X-Y) of the surface 109-1 of the first section 152-1 relative to the angle or pitch of the surface 109-2.

The bending or movement of one section is also described as changing the angle of the x-axis of a section relative to the horizontal and relative to the angle of the x-axis of another section relative to the horizonal.

The plate 150 further comprises recesses 108 provided at each end of the channels 153, 154. Recesses 108 are located between the side walls 106 and the channels 153, 154.

Essentially the first and second ends of the channel 153 are recessed relative to the side walls 106 of the plate by the provision of the recess 108. In the exemplary embodiment, the recess 108 comprises walls that are tapered or slope from the side wall 106 of the plate back to the ends of the channel 152. The recesses 108 may comprise a generally semi-spherical cut out form or u-shaped relative to the top, bottom and side surfaces 109, 110 and 106 of the plate. The recesses 108 are configured to act as the fulcrum of the bending forces between adjacent screw holes when the plate is adapted intra-operatively to match the patient's anatomy. These will allow the bending of the plate to adjust the transverse axis of a first section 152-1 about a recess 108 relative to the transverse axis of a second adjacent section 152-2. In a preferred arrangement the direction of a first section 152-1 may be adjusted about an axis of the recess 108. In a preferred arrangement the direction of a first section 152-1 may be adjusted about a vertical (Z-Z axis) of the recess relative to the axes of the plate (X-X, Y-Y).

The channels 153, 154 are configured to allow for the bending of the plate to provide for intra-operable customisation of the form of the plate to a bone of a patient.

The recesses 108 are similarly configured to allow for the bending of the plate to provide for intra-operable customisation of the form of the plate to a bone of a patient.

As described above the plate 150 is configured to be contoured to a bone in two axes via the trench/channel 153, 154 between the screw holes 151 for maximal fracture fixation. Further advantages includes that the plate is contourable to a bone in-situ as the bone plate is fixed to the bone.

Bending of the bone plate at the channel is affected including by the forces applied at the screw hole as the screw is inserted and advanced into the bone, the male engagement components 166, 115, 116 and female engaging components 156,101, 102, 103, 114 of the locking mechanisms 155, 165 interact and transform the rational force from screw advancement to compressive form of the screw onto the plate—which provides for bending of the plate at the channels.

In effect the screw and screw hole interaction provides a drive mechanism or control means for the bending of the plate as the plate in applied during the course of the operation by the surgeon. As the screw is advanced the screw head features interact as controlled and positioned by the surgeon with the screw hole features of the plate.

The interaction of the screw and plate provides for transfer of forces across the fracture (friction of plate against bone) and through the plate (via screw to plate and back to screw).

The plate can be pre-contoured by the surgeon in the operating theatre by the use of bone plate benders, bone plate pliers or bone plate bending press to relate to the patient's individual anatomy or fracture pattern by using the channels 153 and 154 to act as a fulcrum for the bending forces. There may be some residual offset of the plate from the bone so as the screw is inserted and advanced into the bone, the male and female components of the locking mechanism interact and transform the rotational force from the screw advancement to compressive force of the screw onto the plate. This compressive force may bend the plate at the channels 153 and 154 so that the potential offset from the plate to the bone is reduced resulting in a more anatomical construct. Feedback from the screw through the screw driver (possibly aided by a torque limiter) will allow the surgeon to ensure there is no excessive compression of plate onto the bone and once satisfied the surgeon stops the rotational force of the screw allowing for the male and female components of the locking mechanism to engage causing the constraint.

Referring to the FIG. 18C, it is shown that the bone facing surface 110 comprises a protrusion 111. Protrusion 111 extends downwardly relative to the lower surface 110. Protrusion 111 is located around the screw hole 151. Protrusion 111 may have a generally circular, ring-shaped or cylindrical form. The lower surface 111-1 of protrusion 111 defines the plate to bone interface. In a preferred arrangement, the protrusions 110 comprise a smooth lower surface 111-1.

Protrusions 111 may be of vertical extent (height in the Z direction of the plate) of up to 0.5 mm. Essentially the lower contact surface 111-1 of protrusions 111 may be offset by up to 0.5 mm in the Z-direction relative to the lower surface 110 of the plate. The protrusions 111 may comprise smooth and or rounded surfaces and edges. Referring to the drawings in the exemplary arrangement of the plate 150 as shown in FIG. 21 (B), the side wall 125 of protrusion 111 is arranged at an angle to the surface of the plate 110 or area 113.

By providing and defining a plate to bone contact surface—comprising the lower contact surfaces of the protrusions 111 of the plate 150—it is possible to define a plate to bone contact surface having a contact area that is less that the area of the bone facing surface. The bone to plate contact surface may define a contact area of the order of 40% to 60% of the area of the overall bone facing surface 110. It will be appreciated that while protrusions 111 and bone to plate contact surfaces of the arrangement of the figures are of a generally circular, ring, annular or cylindrical form—protrusions 111 of other suitable alternative form may be provided. The protrusions are centrally located in the sections 152 of the plate and relative to the channels 153, 154.

Overall, the plate arrangement as defined including the plate bone contact surfaces of protrusions 111 provides for a limited contact with the bone (in comparison with other plate arrangements) and which advantageously provides for maintaining periosteal integrity.

As the only plate/bone contact happens in a small areas 111, 111-1 surrounding the screw hole the plate is configured to support conservation of the bones blood supply between the screw holes.

In an alternative arrangement, the plate bone interface may comprise a roughened surface to allow for osteogenesis of the bone onto the plate for increased stability if deemed necessary by the surgeon. The form of the surface defining the plate to bone interface may be varied for different medically indicated requirements.

As noted above the lower side or lower surface 110 of the plate comprises channels 154 recessed relative to the lower surface 110. The bone facing surface may further comprises recessed surface portions 113 provided on both sides of the channels 154. The surface 110 and surface portions 113 are arranged and configured to limit compressive force applied on the bone. The arrangement including recesses 113 acts to allow the periosteal blood supply even in the event that the sections are bent relative to each other or moved or rotated about the channel to an angle relative to each other. Recess 113 provides an area where there is no compression on the periosteum despite the bending of the fulcrum trenches of 107 and 112.

Figure 22A:
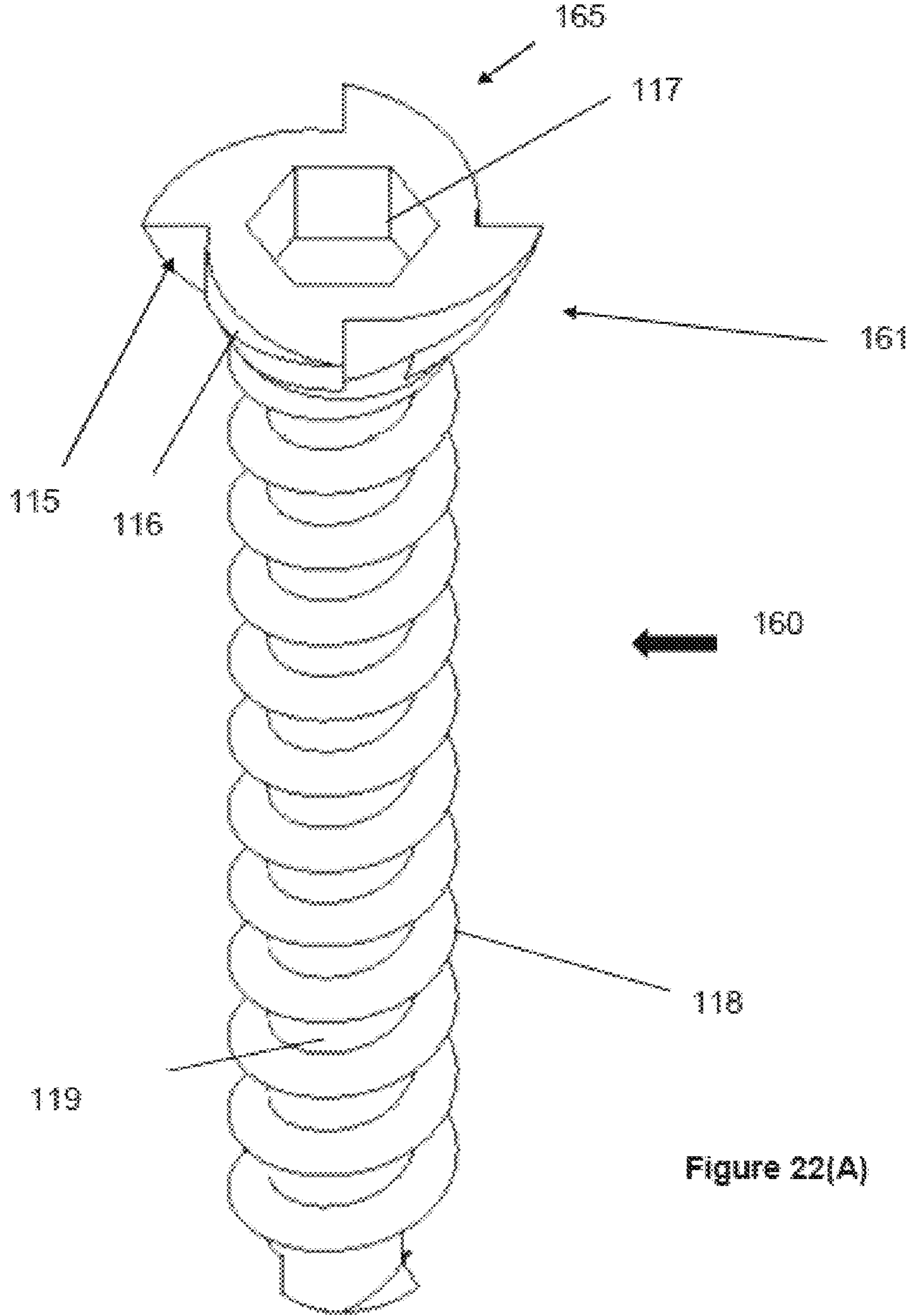
Figure 22B:
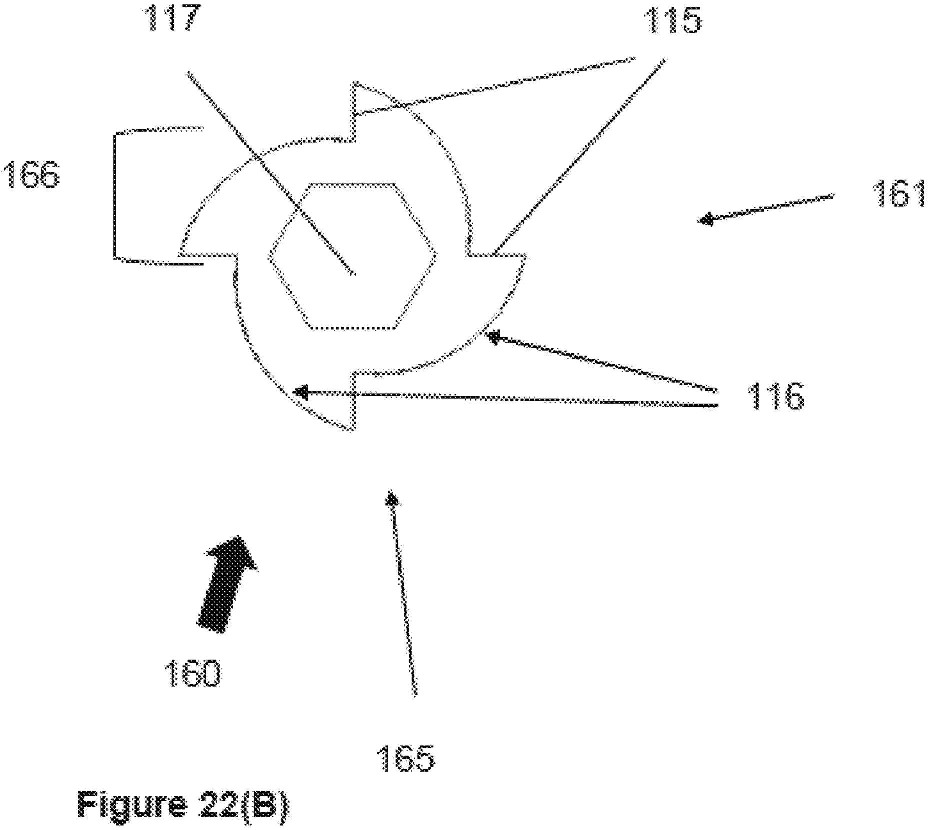
Figures 22C, 22D:
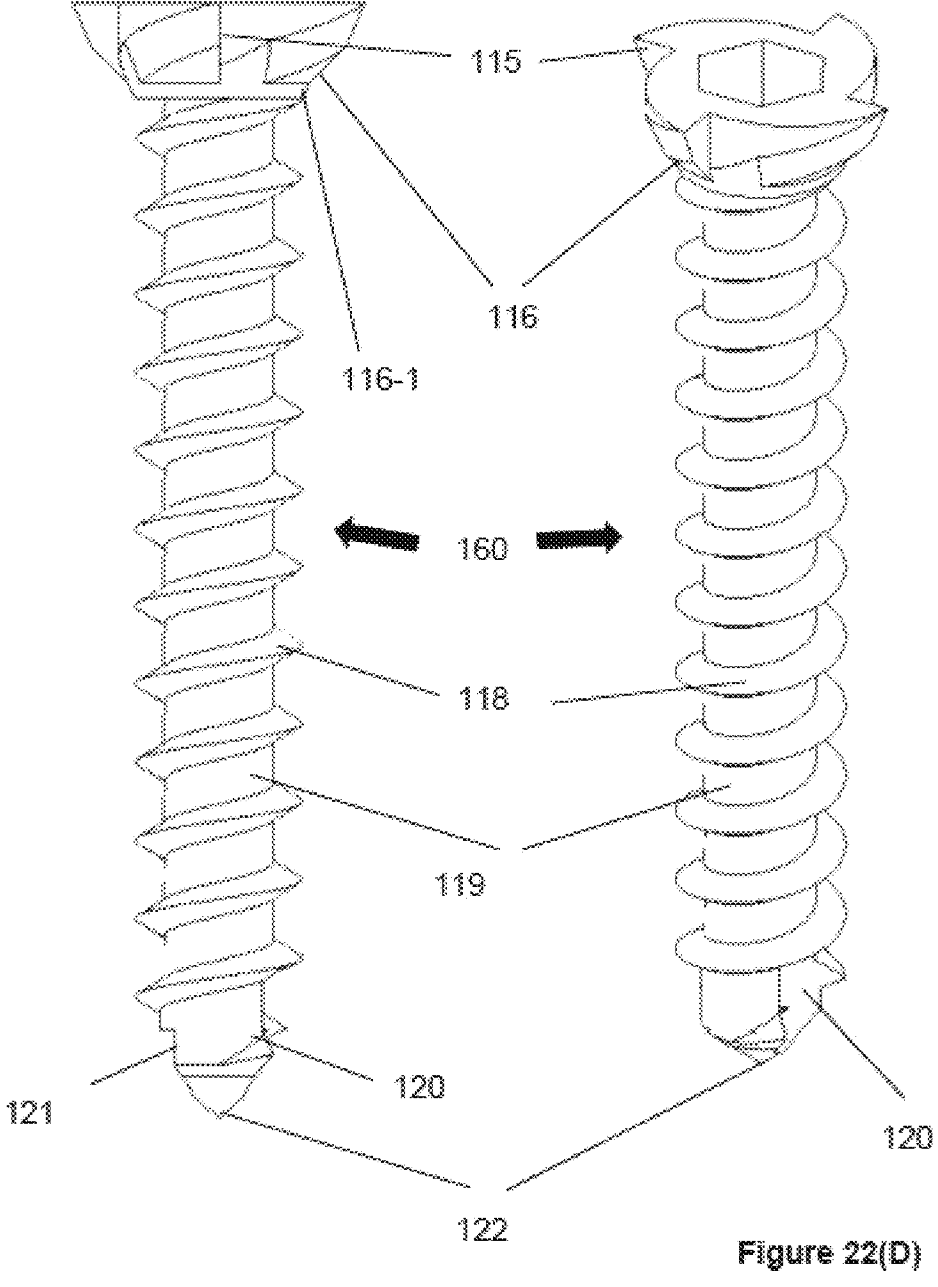

Referring FIG. 22 screw 160 is described with reference to the drawings. Screw 160 comprises screw head 161 comprising a locking mechanism 165. The locking mechanism 165 comprises male engagement components 166 configured to conform to the female engagement components 102, 103 and 114 of the screw hole 151.

In the arrangement of the drawings the screw hole comprises four female engagement features and the screw head comprises four male engagement features. Engagement features 166 of the screw head comprise surface 115 that is arranged to engage surface 102 in the locked position. Walls or wings 116, 116-1 are provided between adjacent engagement surfaces 115. Walls 116, 116-1, 116-2 define a shoulder of the engagement surface of the screw head. The engagement surface 115 of the screw head interacts with the female engagement surface 102 of the screw hole in the plate and prevents the screw from toggling/backing out. The shoulder 116 comprises a sloped or chamfered shoulder of the screw head which interacts with sloped or chamfered face 101 of the plate and around the screw hole features 114.

Indentation 117 in the top of the screw head is configured to allow for insertion of a screwdriver into the screw head to allow for a rotational force to be applied to the screw. A hexagonal indentation is illustrated in the exemplary arrangement of FIG. 21. However, it will be appreciated that any suitable alternative for example star/cross/Philips head or any other screw head configuration can be applied.

The screw comprises treads 118, 119 having an external portion 118. The pitch, angle, and height of the treads can be varied or selected as required. The internal portion 119 of the screw shaft. Again the diameter and other features may be selected as required.

The screw tip 122 may further comprise an indentation or flute 120 which is configured to allow for a self-tapping use of the screw. The indentation or flute 120 comprises a major or larger dimensioned indentation.

The screw tip 122 may further comprise indentation or flute 152 which allows for a self-tapping use of the screw.

The bone plate of the present specification is configured by virtue to the special combination of features to provide periosteal protection. The periosteum is a dense, fibrous connective tissue sheath that covers the bones. The outer layer, made up of collagen fibers oriented parallel to the bone, contains arteries, veins, lymphatics, and sensory nerves. The periosteum makes major contributions to this complex bone-healing process. The periosteum is one source of precursor cells which develop into chondroblasts and osteoblasts that are essential to the healing of bone.

To improve protection for the periosteum, the bone plate 150 comprises elevated areas 111 that protrude relative to the lower surface 110 of the bone plate 150 are configured be the point of contact between the plate and the bone thus decreasing the area of surface contact between the plate and the bone. The arrangement having reduced surface area contact between the bone plate and the bone assists in reducing periosteal damage. The area of the contact areas 111 may be configured to between 40-60% of the overall area of the surface of the plate. Accordingly, the area of plate to bone contact for the plate 100 is reduced relative to plate to bone contact between a conventional compression plate and the bone.

The channel or trench features 153, 154 are configured to allow for customisation of the bone plate to the form of the bone intraoperatively. The channel features define integrated specific bending points at the mid-point between the screw holes. The channel 153 (having base 107 and side walls 104, 105) on the superior surface 109 and the channel 154 (having base 112 and side walls 123, 124) on the inferior side 110 are provided as two channels or trenches on the plate surfaces. Each channel is configured to act as the bending point when pressure is applied at either side of the trenches (i.e. bone plate benders, bone plate pliers or bone plate bending press). These two channels effectively allow the plate 100 to bend, in effect the relative positions and angles of the surfaces of the sections either side of the channels 153 and 154 is changeable) in the inferior and superior planes 109, 110. Accordingly, these features of the bone plate 100 are configured to allow the surgeon to customise the plate to the anatomy of the bone/fracture to optimise the structural integrity of the fixation.

The plate further comprises recesses 108 which are configured to allow for bending of plate in the medial/lateral plane (Y-Y). The recesses 108 are of a generally semi-circular, 108. The provision of the recesses 108 in the lateral side edges of the channels located at the mid-point between adjacent screw holes 151 allows for further customisation of the position and surface arrangement of the plate intraoperatively.

In one example, example 1, a plate according to an exemplary arrangement of the specification is configured as a straight plate that extends a length L in the X-X axis direction of the order of 100 mm, having a thickness or height profile H2 of 2 mm between the upper surface 109 and lower surface 110 and H1 of the order of 2.5 mm between surface 109 and surface 111, and having a lateral dimension or width W in the Y-Y direction of the order of 10 mm. Another example—example 2—according to an exemplary arrangement of the specification is comprised of a ⅓ tubular plate to further match the contour of bones.

The bone plate and screw may comprise any suitable bio-compatible material including for example Titanium or stainless steel.

The width and thickness of the plate can be altered according to the requirement of the different bones to be treated including to match the increased loads involved in treating fractures of these different bones (e.g. femur, tibia, humerus, metatarsals, calcaneus, radius, ulna, spinal, maxillofacial and other bones). While the bone plate of the exemplary arrangement of the specification has a generally rectangular form or shape, it will be appreciated that the form of the bone plate according to the present specification can be adapted for various bones. The configuration or form of the plate may be varied so that the head of the plate is in a T-shape, L-shape, Y-shape or any other shape that is appropriate for fracture fixation of an appropriate bone with a shaft portion which is secured to the metaphysis or diaphysis of the bone.

With reference to and by virtue of the arrangement of the four female and male engagement features circumferentially around the screw hole, the surgeon only has to turn the screw a quarter rotation to advance the screw to the next locking position and the advancement of the screw with this quarter rotation would not provide too much compression of the plate to the bone.

114, 114-1, 14.2 are the sloped walls of the female wings 114 of the locking mechanism of the plate 150 and these engage with the sloped edge of the male components of the screw heads 116. 114.1 is the straight inferior portion of the female locking mechanism and provides a space for the inferior portion of the male locking components (116) to fit.

Figure 24A:
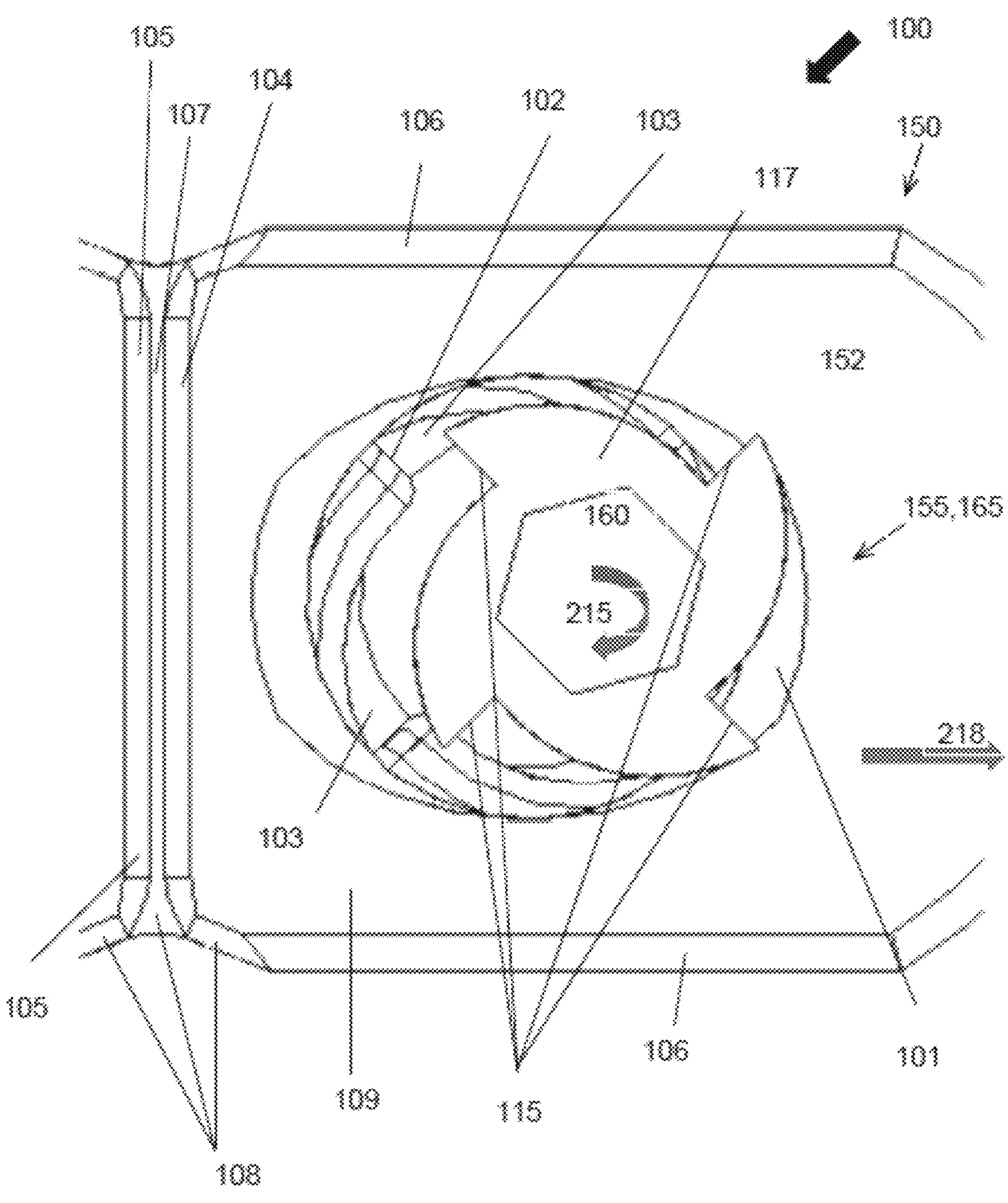
FIGS. 24(*a*) and 24(B) provide respectively a plan view from above and a side plan view of an exemplary arrangement of system 100 of the specification including plate 150 of FIGS. 20 and 21 and screw 160 of FIGS. 22 and 23; the drawings show the screw head arranged in proximity to the screw hole as the screw is being advanced through the screw hole and as the features of the locking mechanisms of the screw hole and screw are brought close together and begin to interact.
Figure 24B:
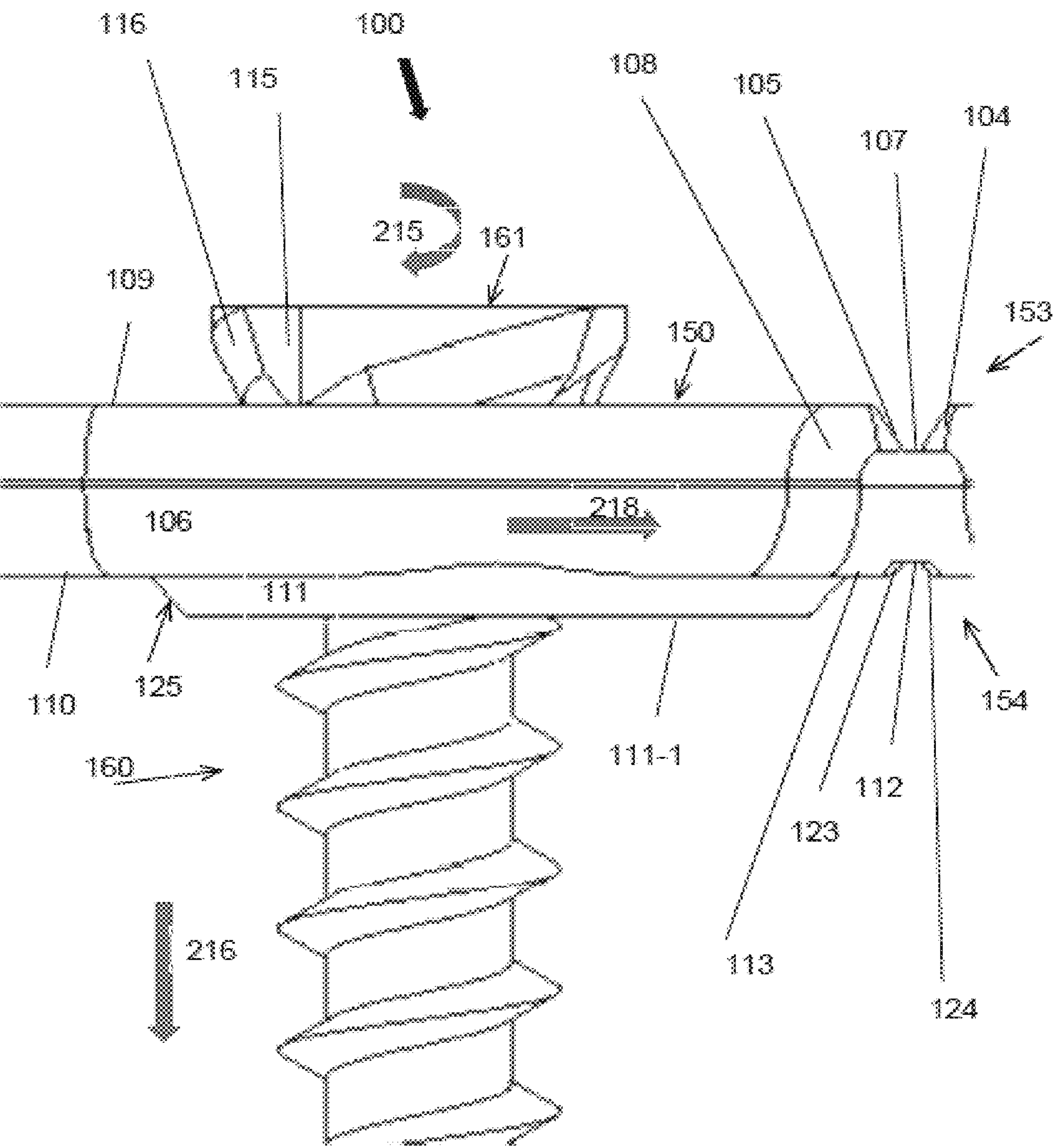
Figure 25A:
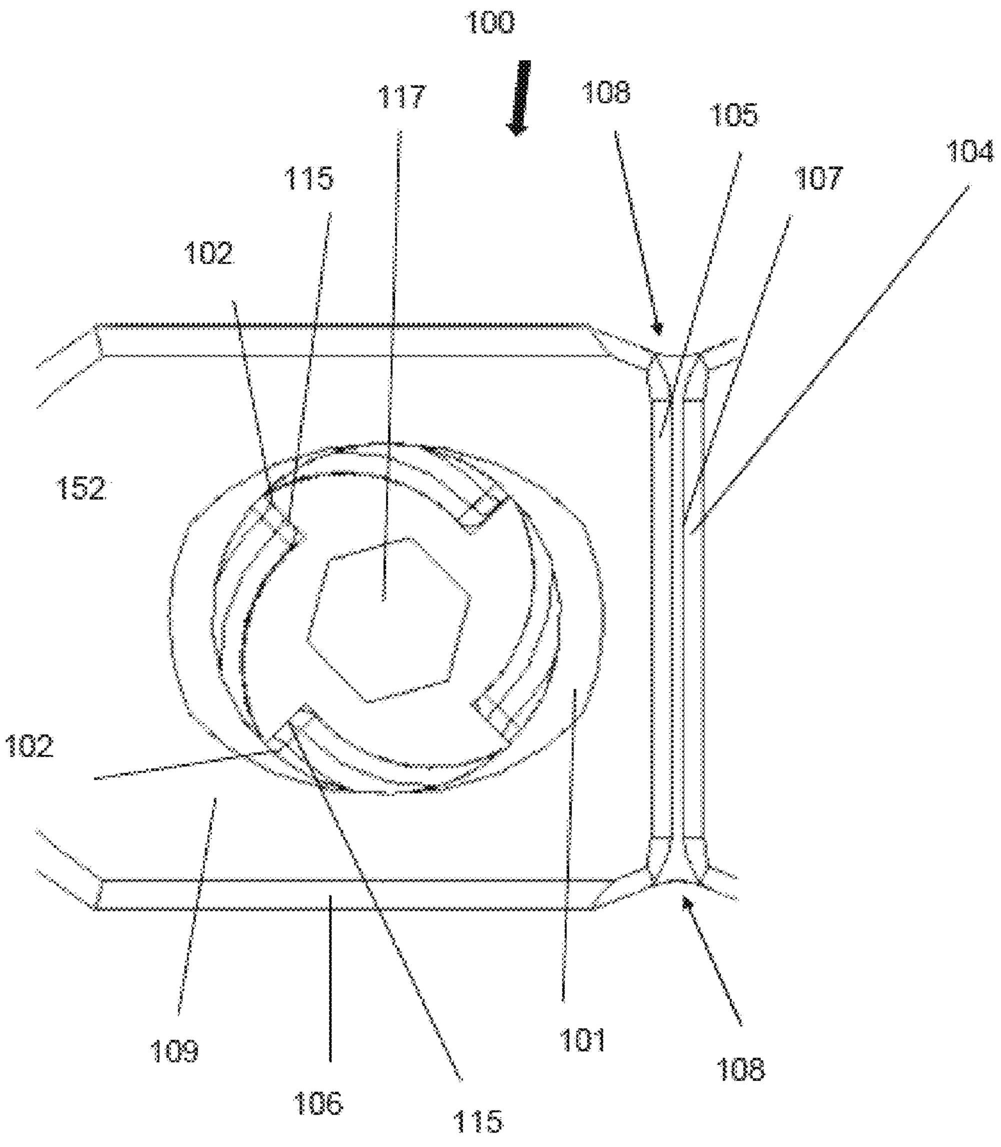
FIGS. 25(*a*) and 25(B) and 25(C) are top plan, side plan and perspective views of the system 100 of FIGS. 20 to 24 with the screw 160 locked in plate in the plate 150.
Figure 25B:
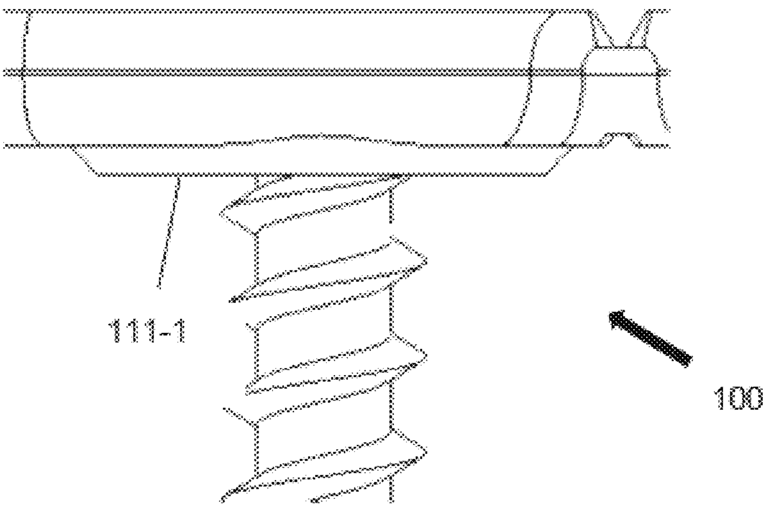
Figure 25C:
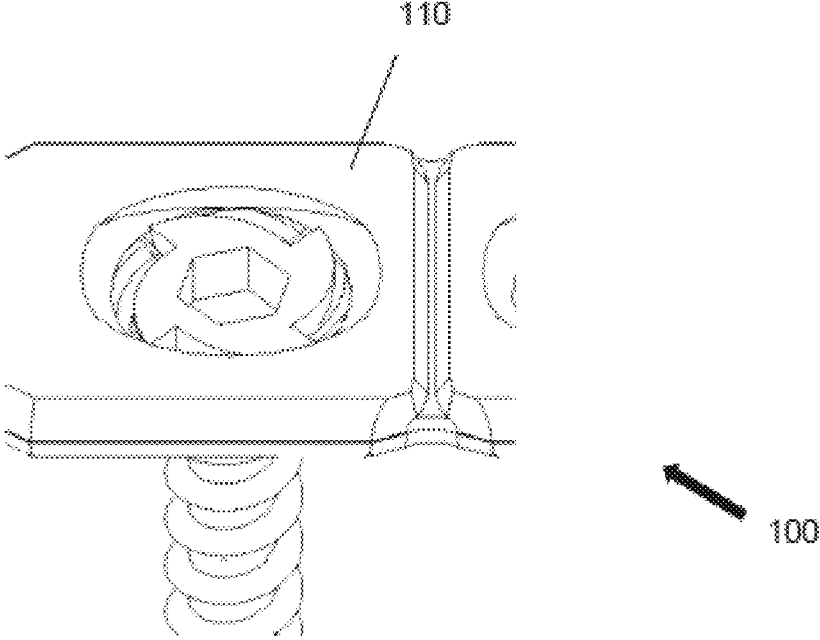

Referring to FIGS. 24(A) and 24(B), exemplary forces applied to the screw and plate when the screw is positioned in the eccentric position are described. Force (arrow) 215 show the right hand rotation of the screw 160 and force 216 shows the resultant and subsequent advancement of the screw into the bone by the action of the screw threads 118. The screw is advanced to the point that the shoulder of the screw 116 interacts with the chamfer 101 of the plate 150 and force 218 shows the resultant movement of the plate 150 as the screw is advanced into the screw hole 151 thus closing down the fracture gap 30.

Figure 27:
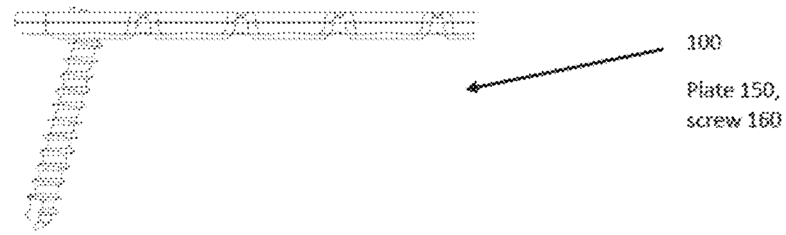
FIGS. 27 (A) to (I) show a variety of illustrations of the system 100 of FIGS. 20 to 26 having screws 160 arranged an angles relative to the plate 100 to provide compression as required, FIGS. 27(A), (B), (C) and (D) are side, top, side plan views and a perspective view from above of a screw engaged with a plate at 15 degrees laterally, FIGS. 27 (E), (F), (G), (H) and (I) are side, and top plan views, and perspective views from the side, above and below showing 6 screw engaged with the plate at 15 degrees in varying planes/orientations.
Figure 27:
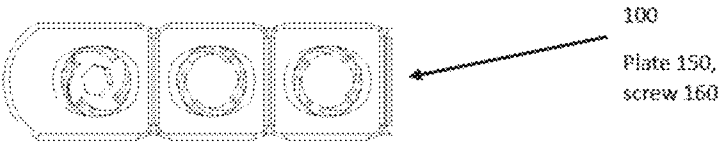
Figure 27C:
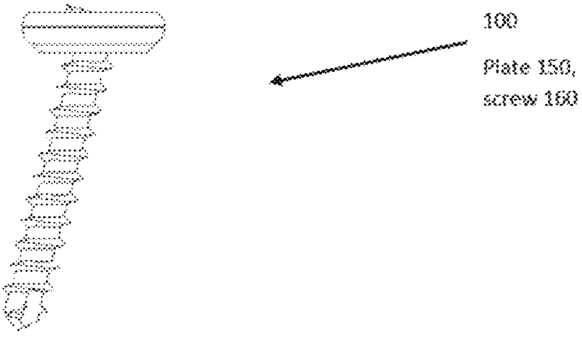
Figure 27G:
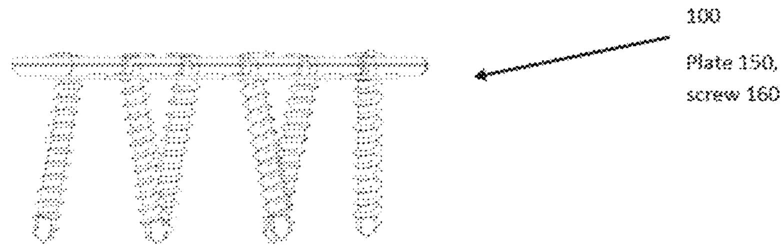
Figure 27:
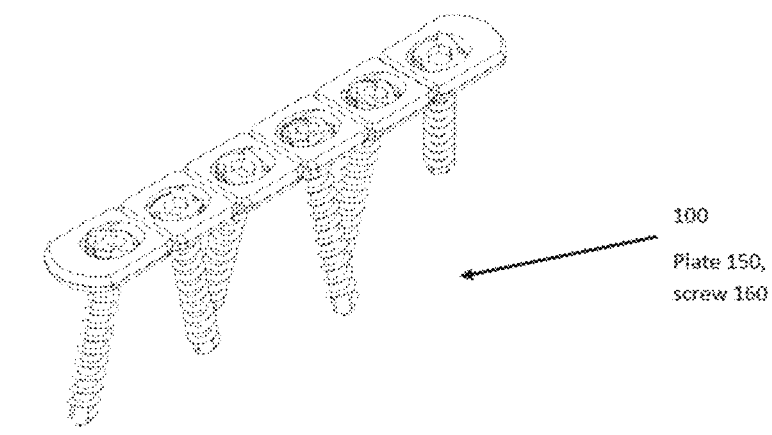
Figure 27:
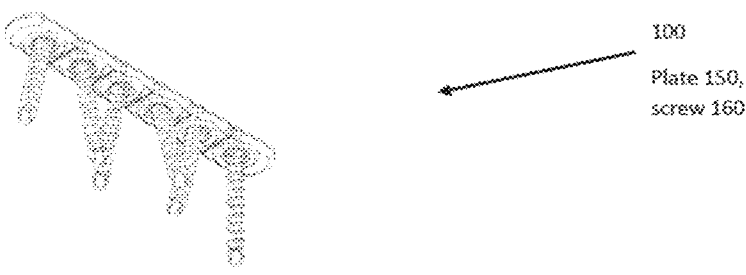

FIG. 27(A) to 27 (I) show screws 160 inserted at angles relative to plate 150 of exemplary arrangement of system 100. These images show the various angles that the screws can be inserted into the plate. This poly-axial ability is key for the surgeon to be able to insert the screws into the plate and bone to allow for maximal customisation of the plate bone complex due to the variations in the patients anatomy and fracture pattern. This advantageously provides for and supports better maintenance of reduction of the fracture and a superior fixation construct.

Figure 26:
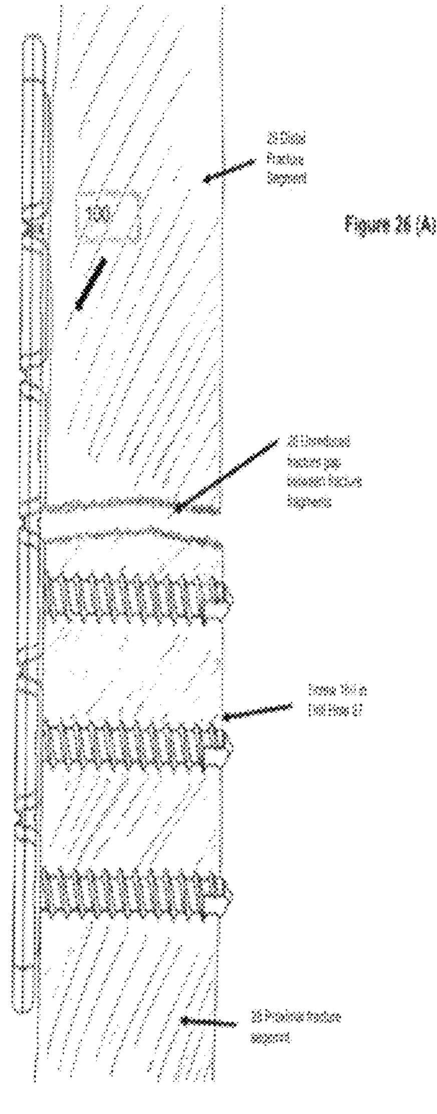
FIG. 26(A) is a cross-section view of a plate 150 in place at a fracture and illustrates the position relative to the fracture
FIGS. 26(B) to (G) are imaging show the progression of fixing of the system 100 at the fracture including location of the place, drill holes, screws and illustrating compression.
Figure 26B:
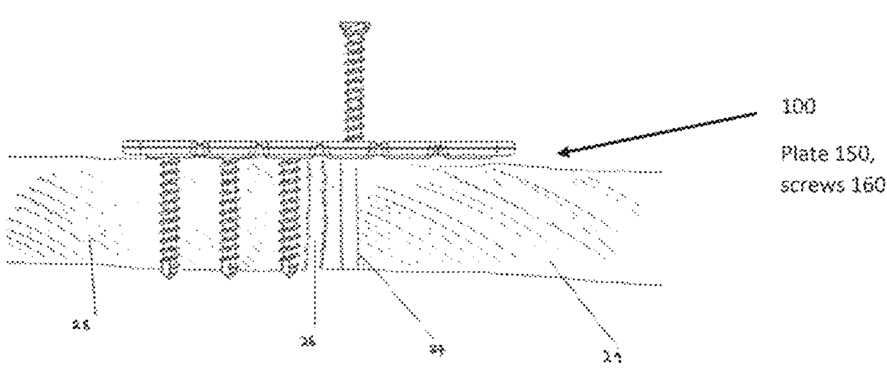
Figure 26C:
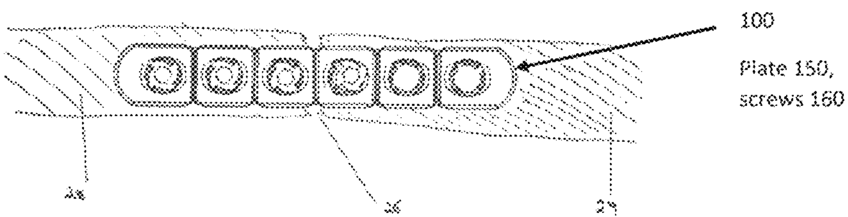

Referring to FIGS. 26(*a*) to 26 (*g*), a series of cross-sectional and top plans views shown which illustrate an exemplary method of application of the system 100 to a bone and relative to a fracture. In these drawing features of the bone including the following unreduced fracture gap 26 between two fracture fragments. Drill hole 27, eccentric from the screw hole. Proximal fracture segment 28 and distal fracture segment 29. In FIGS. 26(*c*) to 26(*g*) a reduced fracture 30 between two fracture segments, is shown. With reference to the drawings location of the plate and screws relative to the fracture is shown.

Figure 26D:
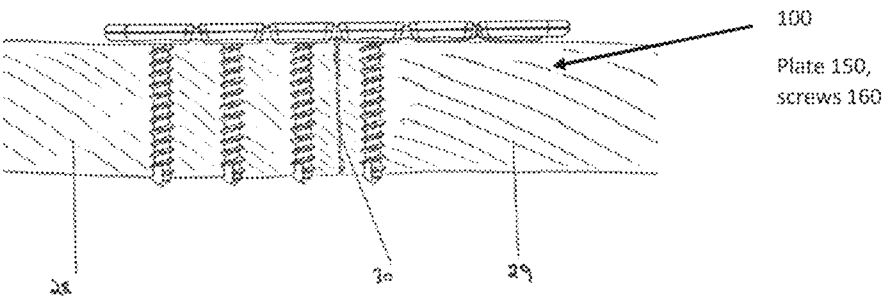
Figure 26E:
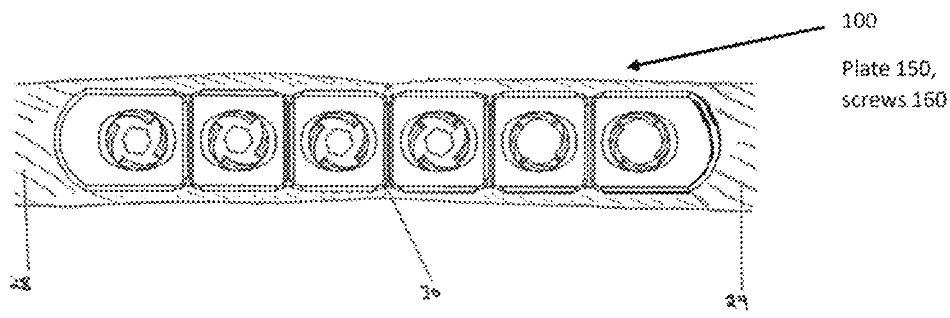
Figure 26F:
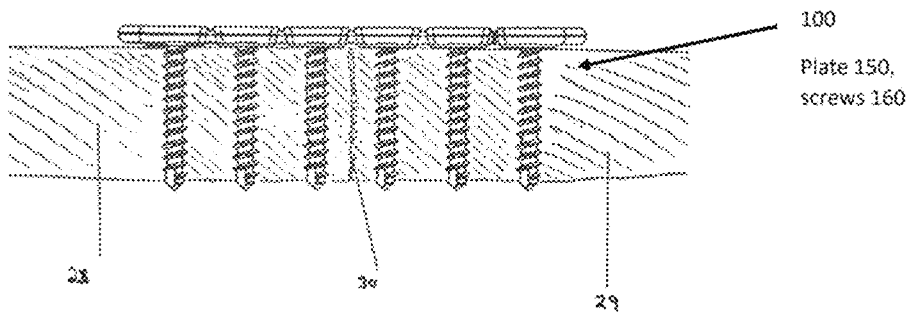
Figure 26G:
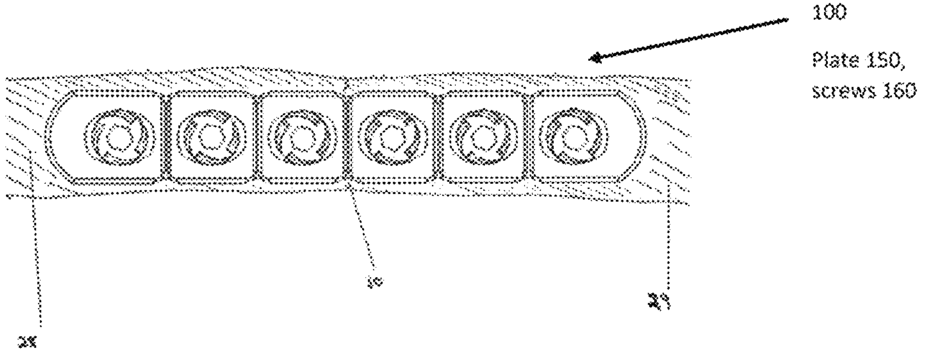

FIGS. 26(*a*) to 26(*g*) illustrate of fracture gap reduction provided by use of the system 100 including of the plate and screw complex if the distal screw (first +/−second screw after the fracture) are placed in an eccentric position. FIG. 26(*a*) shows a lateral cross-section of the plate and bone. Three screws are inserted into the proximal segment of the fractured bone and fracture gap 26 is evident. FIG. 26(*b*) shows a further lateral image and a drill hole in the eccentric position 27 is placed in the distal segment of the fracture 29. A screw placed in the eccentric position is observed in fourth screw hole of the plate (first screw hole of the distal segment of the fracture). The fracture gap 26 is still evident. FIG. 26 (C) is a top down view of what is observed in FIG. 26 (B). FIG. 26(D) is a lateral cross-sectional view of the plate bone complex. The fourth screw is advanced into the first screw hole of the distal fragment. The shoulders of the screw 116 engage with the chamfer 101 or recessed area 101 of the plate 150 to pull the proximal segment of the fracture to allow centric placement of the screw head in the screw hole of the plate. This results in closure/elimination of the fracture gap 30. FIG. 26 (E) is a top plan view of FIG. 26 C. FIGS. 26 (F) and (G) are top down and lateral views of the plate 150 inserted into bone with all 6 of the screw holes 151 filled with screws 160. No fracture gap is evident.

Referring to the drawings and FIG. 26 in particular, the specification provides a method of operating the system 150 to provide a combination of dynamic and compression functions to allow for corrective surgery by bone compression, including:

- identify the Fracture/osteotomy/gap in bone;
- retract soft tissue;
- plate is compared to patient's anatomy and adjusted to fit by bending the plate at point equidistant between two adjacent screw hole—using a suit device;
- if compression at the gap site is desired a drill hole should be made in the bone in an eccentric position (off-centre);
- the width of the bone is measured and desired screw length chosen'
- the screw is then advanced in a clock-wise (right-handed) direction;
- the shoulder of the screw head will contact the slope of the plate and as it advances further it will move the plate longitudinally (and therefore close the gap in the bone) to allow it to be in a centric position;
- the screw is over tightened to the desired tension by the surgeon, a torque limited maybe incorporated into the screwdriver preventing over tightening;
- the screw is advanced and the male components of the screw head engage with the female components of the plate, the male components will interact with the female components and lock into place.

In an optional step, relating to the method, should a screw need to be removed—compression of plate to the bone should be applied (via clamp) to loosen the locking mechanism and the screw is turned clock-wise (right hand direction) for a quarter turn to disengage the locking mechanism. A custom fit screwdriver sleave is advanced over the screw once all the male components have disengaged and this sleave will prevent the male screw components from re-engaging with the female components and allow for removal of the screw. The screw is removed by rotating it anti-clockwise (left hand) direction.

Benefits and advantages of the present disclosure include the following. Patients have a decreased risk of non-union/failure and need thus need for re-operation. Also, the patient healing time is decreased, which evidently results in a quicker return to normal daily activities, i.e. work. The device of the present disclosure is very user friendly which is of benefit to medical staff. Bending of the bone plate at the channel is affected including by the forces applied at the screw hole as the screw is inserted and advanced into the bone, the male engagement components 166, 115, 116 and female engaging components 156,101, 102, 103, 114 of the locking mechanisms 155, 165 interact and transform the rational force from screw advancement to compressive form of the screw onto the plate—which provides for bending of the plate at the channels.

In effect the screw and screw hole interaction provides a drive mechanism or control means for the bending of the plate as the plate in applied during the course of the operation by the surgeon. As the screw is advanced the screw head features interact as controlled and positioned by the surgeon with the screw hole features of the plate.

The interaction of the screw and plate provides for transfer of forces across the fracture (friction of plate against bone) and through the plate (via screw to plate and back to screw).

The plate can be pre-contoured by the surgeon in the operating theatre by the use of bone plate benders, bone plate pliers or bone plate bending press to relate to the patients individual anatomy or fracture pattern by using the channels 153 and 154 to act as a fulcrum for the bending forces. There may be some residual offset of the plate from the bone so as the screw is inserted and advanced into the bone, the male and female components of the locking mechanism interact and transform the rotational force from the screw advancement to compressive force of the screw onto the plate. This compressive force may bend the plate at the channels 153 and 154 so that the potential offset from the plate to the bone is reduced resulting in a more anatomical construct. Feedback from the screw through the screw driver (possibly aided by a torque limiter) will allow the surgeon to avoid the application or effects of any excessive compression of plate onto the bone and once satisfied the surgeon stops the rotational force of the screw allowing for the male and female components of the locking mechanism to engage causing the constraint.

Advantages of the arrangements of the bone plates 150 and 1 and screws 160 (system 100 and system 500) include the following. When in place the system (plate and screw) maintains fracture reduction by compressing the plate to the bone in a locked fashion. The system (plate and screw) allows for fracture reduction via eccentric screw position. No need for a lag screw. Transfers forces across the fracture (friction of plate against bone) and through the plate (via screw to plate and back to screw). The plate can be contoured to bone in two axes via the trench/channel between the screw holes for maximal fracture fixation. The plate can be contoured to the bone also via bending about the recesses. The system is contourable in-situ during an operation. Screws can be inserted at an any angle up to but not limited to 20 degrees. There is no requirement for a fixed angle locking drill guide. The arrangement of the plate provides for a limited contact with the bone to maintain periosteal integrity. The system provides that only one screw head type is needed for interaction with the plate and screws of different lengths may be provided.

The arrangement of the specification allows for minimally invasive osteosynthesis.

Further advantages include that the arrangement of the specification provides for:

- Possible use of variable angle drill guide;
- Possible use of Eccentric and centric drill guides;
- Possible use of benders in two planes;
- Possible use of torque screwdriver with custom sleeve; and
- Possible use of customised clamp (one side to fit into screw hole) to reduce the plate to bone.

The bone plate of the present disclosure allows for compression in the axial plane (reducing the fracture) and in the perpendicular plane (compressing plate to bone). It can be contourable (i.e. bent to a shape, unlike standard locking plates) and it can prevent periosteal ischaemia (damage) at the fracture site. Periosteal ischaemia is a known contributor to facture non-unions, as the only plate/bone contact happens in a small area surrounding the screw hole allowing for conservation of the bones blood supply between the screw holes.

The bone plate of the present disclosure facilitates the creation of a screw/plate complex, independent of the plate/bone interface.

In one aspect, the present disclosure relates to a locking system comprising a locking bone plate for fracture fixation and a screw, adapted for engagement in the locking bone plate.

The screw locking heads are provided in two sizes/dimensions, such that in one version, the screw engages with the locking plate in a plush fit to the locking plate and in the second version, the screw engages with the locking plate in an offset arrangement so as to allow some movement in the screw plate complex i.e. in the locking system of the present disclosure. This allows the surgeon to decide if the fracture needs rigid fixation or some degree of micromotion for optimal healing. On the under surface of the plate, the plate comprises a raised area around the screw hole to allow for preservation of the periosteum of the bone between the adjacent screw holes. This raised area reduces the contact area of the plate to bone by between 40 and 60% and thus spares the interval periosteum from compression and ultimately ischaemia. This should increase the healing potential of the fracture in comparison to conventional compression plates.

The area between adjacent screw holes is malleable to allow for customisation by the surgeon intra-operatively for optimal fracture fixation. The screw head comprises a tapered shoulder to allow for compression at the fracture site if placed in an eccentric position.

The system (100) comprising a dynamic locking bone plate and screw provide a plate and screw complex for fracture fixation. The plate comprises a plurality of screw holes, each screw hole adapted to receive a screw. The screw threads allow for insertion into bone with compression of the plate to bone and the four male components on the screw head allow for the screws to be locked into place in the plate once they interact with the female components of the plate. The screw locking heads will come in two form, one plush fit to the locking plate and the other offset to allow some movement in the screw plate complex. On the under surface of the plate, the plate comprises a raised area or protrusion defining the bone to plate contact surface. The area between adjacent screw holes is adapted to allow for customisation by the surgeon intra-operatively for optimal fracture fixation. The screw head comprises a tapered shoulder to allow for compression at the fracture site if placed in an eccentric position.

It should be noted that various changes and modifications to the presently preferred embodiments described herein will be apparent to those skilled in the art. Such changes and modifications may be made without departing from the spirit and scope of the present disclosure and without diminishing its attendant advantages. Further, references throughout the specification to "the disclosure" are nonlimiting, and it should be noted that claim limitations presented herein are not meant to describe the disclosure as a whole. Moreover, the disclosure illustratively disclosed herein suitably may be practiced in the absence of any element which is not specifically disclosed herein.

The invention claimed is:

1. A bone fixation system (500, 100) configured to provide a combination of dynamic and compression functions to allow for corrective surgery by bone compression, the system comprising:

- a bone plate (50, 150) having an upper external surface (109) and a lower bone facing surface (110) and at least two screw holes (151), and
- associated bone screws (160);
- the bone plate and screws comprising corresponding engagement elements (156, 166);
- each bone screw (160) having a head comprising screw engagement elements (166);
- each bone plate screw hole (151) comprising plate engagement elements (156) which are monolithic with the bone plate (150), each plate engagement element (156) comprising a stop surface (102) configured to abut in a ratchet engagement with a corresponding screw engagement element (166) as the screw is advanced to provide screw-to-plate-constraint and prevent backing out of the screw;
- the bone plate (50, 150) further comprising recesses (2, 108, 153, 154) located between two adjacent screw holes, the recesses (2, 108, 153, 154) configured to allow for bending of the plate to provide for intra-operable customisation of a form of the plate to a bone of a patient, the recesses comprising a first transverse channel (153) in the upper external surface (109) and a second transverse channel (154) in the lower bone facing surface (110), the first and second channels being arranged back-to-back transversely across the plate; and further comprising one or more recessed areas (101) surrounding the screw holes in the upper external surface (109) of the plate, wherein the recessed areas (101) are sloped and configured to allow the screws (160) to be placed eccentrically into the bone and allow for compression at a fracture site once contact is made between the screw head and plate.

2. The system of claim 1, wherein the first and second channels are configured to allow bending of the plate about a central axis of the channel to change a pitch of the surface of a first section of the plate relative to that of an adjacent section of the plate.

3. The system of claim 1, wherein the bone plate (150) further comprises protruding elements (111) protruding relative to the lower bone facing surface (110) of the plate (150) to define plate to bone contact surfaces for contact between the plate (150) and bone.

4. The system of claim 1, wherein the recesses (101) are configured such that the screws (160) are insertable at an angle of up to substantially 20 degrees.

5. The system of claim 1, the screw head (161) comprising a tapered shoulder (116) to allow for compression at a fracture site if placed in an eccentric position.

6. The system of claim 1, wherein an area between adjacent screw holes is malleable to allow for customisation by a surgeon intra-operatively for optimal fracture fixation.

7. The system of claim 1, wherein each bone screw comprises an indent in a tip thereof configured to provide a self-tapping option during insertion.

8. The system of claim 1, each bone screw comprising at least two protruding screw engagement elements and the plate comprising at least two plate engagement elements configured to inter-engage with the screw engagement elements.

9. A method of operating the bone fixation system of claim 1 to provide a combination of dynamic and compression functions to allow for corrective surgery by bone compression including:

- identifying a fracture/osteotomy/gap in bone;
- retracting soft tissue;
- comparing the bone plate to a patient's anatomy and adjusting a fit of the plate by bending the plate at a point equidistant between two adjacent screw holes using a suitable device;
  - if compression at the gap site is desired, drilling a hole in the bone in an eccentric position (off-centre);
  - measuring a width of the bone and choosing a desired screw length;
  - advancing a screw using a screwdriver in a clock-wise (right-handed) direction;
  - contacting a shoulder of the screw head with a slope of the plate and as it advances further, moving the plate longitudinally to close the fracture/osteotomy/gap in the bone to allow it to be in a centric position;

tightening the screw to a desired tension by the surgeon, wherein a torque limiter is incorporated into the screwdriver preventing over tightening; and causing the screw engagement elements of the screw head to engage with the plate engagement elements of the plate, such that the screw engagement elements interact with the plate engagement elements to lock into place.

10. The system of claim 1, wherein the first and second channels (153, 154) are located midway between the adjacent screw holes (151).

11. The system of claim 1, wherein the bone facing surfaces comprises a raised area around the screw hole configured to contact the bone and configured to allow for preservation of a periosteum of the bone between the adjacent screw holes.

12. The system of claim 1, wherein the bone plate (150) further comprises side recesses (108) located at side edges of the plate at the first and second ends of the channels (153, 154).

13. The system of claim 1, wherein the bone plate (150) further comprises side recesses (108) located at side edges of the plate at first and second ends of the channels (153, 154), wherein a combination of the channels (153, 154) and the side recesses (108) is configured to allow for bending of the plate in two axes.

* * * * *